(12) United States Patent
Swayze et al.

(10) Patent No.: US 8,974,400 B2
(45) Date of Patent: Mar. 10, 2015

(54) INSTRUMENT FOR APPLYING THERAPEUTIC CELLS, WITH DISTAL PORTION FOR PROCESSING THERAPEUTIC CELLS

(75) Inventors: Jeffrey S. Swayze, Hamilton, OH (US); Mark H. Ransick, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 971 days.

(21) Appl. No.: 12/777,472

(22) Filed: May 11, 2010

(65) Prior Publication Data
US 2011/0282241 A1 Nov. 17, 2011

(51) Int. Cl.
| | | |
|---|---|---|
| A61B 10/00 | (2006.01) |
| A61M 37/00 | (2006.01) |
| A61M 25/00 | (2006.01) |
| A61M 5/32 | (2006.01) |
| A61B 17/32 | (2006.01) |
| A61B 10/02 | (2006.01) |

(52) U.S. Cl.
CPC ......... *A61B 10/0275* (2013.01); *A61B 10/0283* (2013.01)
USPC ........... 600/564; 600/562; 600/563; 600/567; 604/82; 604/264; 604/272; 606/167; 606/170; 606/184

(58) Field of Classification Search
USPC .......... 600/562–567, 569–571; 606/167, 170; 604/28, 82, 152, 263, 264, 267, 272
See application file for complete search history.

(56) References Cited

U.S. PATENT DOCUMENTS

| | | |
|---|---|---|
| 3,996,935 A | 12/1976 | Banko |
| 5,526,822 A | 6/1996 | Burbank et al. |
| 5,694,951 A | 12/1997 | Bonutti |
| 5,827,217 A * | 10/1998 | Silver et al. ............ 604/28 |
| 6,071,284 A | 6/2000 | Fox |
| 6,086,544 A | 7/2000 | Hibner et al. |
| 6,990,982 B1 | 1/2006 | Bonutti |

(Continued)

FOREIGN PATENT DOCUMENTS

WO   WO 2007/008710   1/2007

OTHER PUBLICATIONS

International Search Report and Written Opinion dated Sep. 12, 2011 for Application No. PCT/US2011/035891.

(Continued)

*Primary Examiner* — Devin Henson
(74) *Attorney, Agent, or Firm* — Frost Brown Todd LLC

(57) ABSTRACT

A tissue harvesting and processing apparatus comprises a body and a distally extending needle. The needle includes an aperture configured to receive tissue. A tissue cutting member is movable relative to the needle to sever a specimen from tissue protruding through the aperture. The tissue cutting member is further operable to mince the severed tissue specimen. The minced tissue may be mixed with a medical fluid component contained in a reservoir. A plunger may expel the medical fluid mixture from the needle. An applier tip may be coupled with the needle to facilitate administration of the medical fluid mixture at a target site in a patient. The needle may comprise a cannula with a needle adapter, which be removed from the cannula to allow the applier tip to be coupled with the cannula. The tissue cutting member may comprise a perforated disc or tube with inwardly projecting blades.

19 Claims, 18 Drawing Sheets

(56) References Cited

U.S. PATENT DOCUMENTS

| | | | |
|---|---|---|---|
| 7,094,233 B2 * | 8/2006 | Desinger | 606/45 |
| 7,115,100 B2 | 10/2006 | McRury et al. | |
| 7,442,171 B2 | 10/2008 | Stephens et al. | |
| 7,465,278 B2 * | 12/2008 | Cicenas et al. | 600/565 |
| 7,611,473 B2 | 11/2009 | Boock et al. | |
| 7,771,754 B2 * | 8/2010 | Memar | 424/574 |
| 7,806,834 B2 * | 10/2010 | Beckman et al. | 600/566 |
| 7,806,871 B2 * | 10/2010 | Li et al. | 604/164.06 |
| 2004/0078090 A1 | 4/2004 | Binette et al. | |
| 2004/0193071 A1 | 9/2004 | Binette et al. | |
| 2005/0038520 A1 | 2/2005 | Binette et al. | |
| 2005/0113736 A1 | 5/2005 | Orr et al. | |
| 2005/0125077 A1 | 6/2005 | Harmon et al. | |
| 2006/0074345 A1 | 4/2006 | Hibner | |
| 2006/0253069 A1 | 11/2006 | Li et al. | |
| 2007/0060935 A1 * | 3/2007 | Schwardt et al. | 606/170 |
| 2008/0071385 A1 | 3/2008 | Binette et al. | |
| 2008/0214955 A1 | 9/2008 | Speeg et al. | |
| 2008/0234715 A1 | 9/2008 | Pesce et al. | |
| 2008/0311219 A1 | 12/2008 | Gosiewska et al. | |
| 2010/0160819 A1 | 6/2010 | Parihar et al. | |
| 2012/0101472 A1 * | 4/2012 | Schroeder et al. | 604/500 |

OTHER PUBLICATIONS

U.S. Appl. No. 12/483,305, filed Jun. 12, 2009, Hibner et al.
International Search Report dated Oct. 19, 2011 for Application No. PCT/US2011/035883.
Written Opinion dated Oct. 19, 2011 for Application No. PCT/US2011/035883.

\* cited by examiner

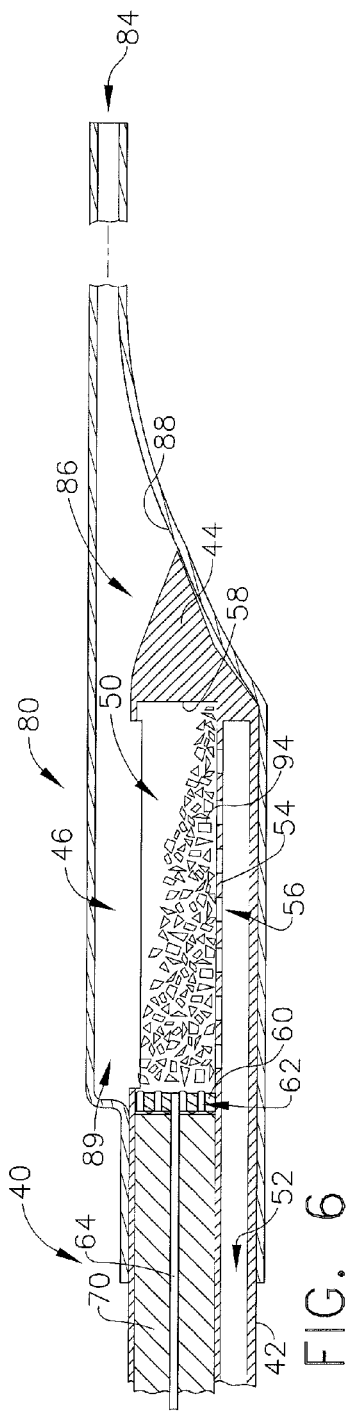
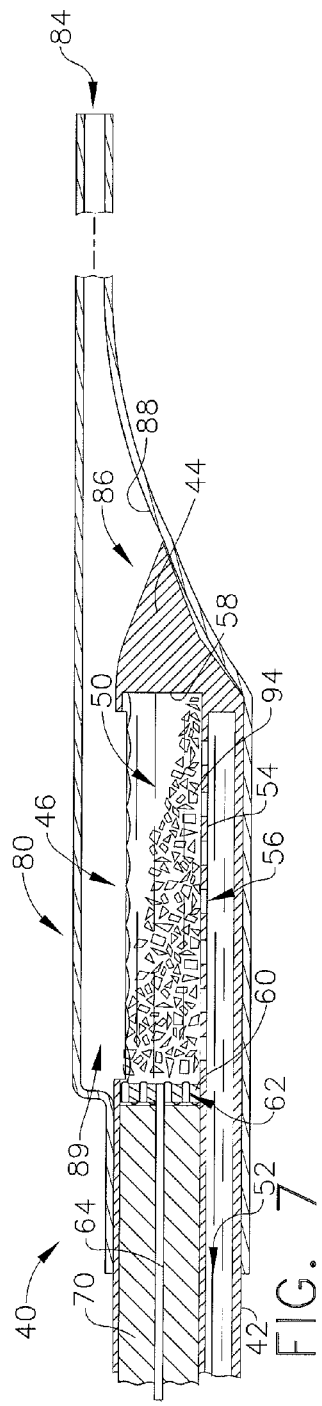
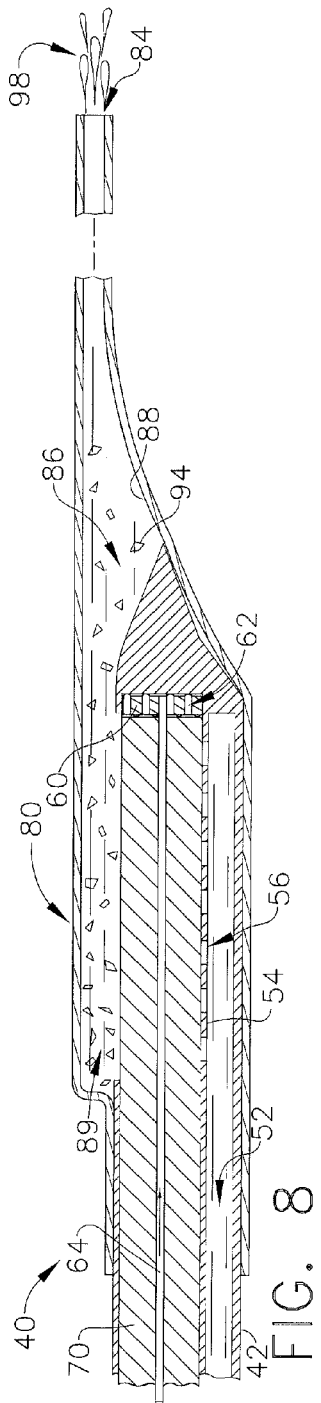

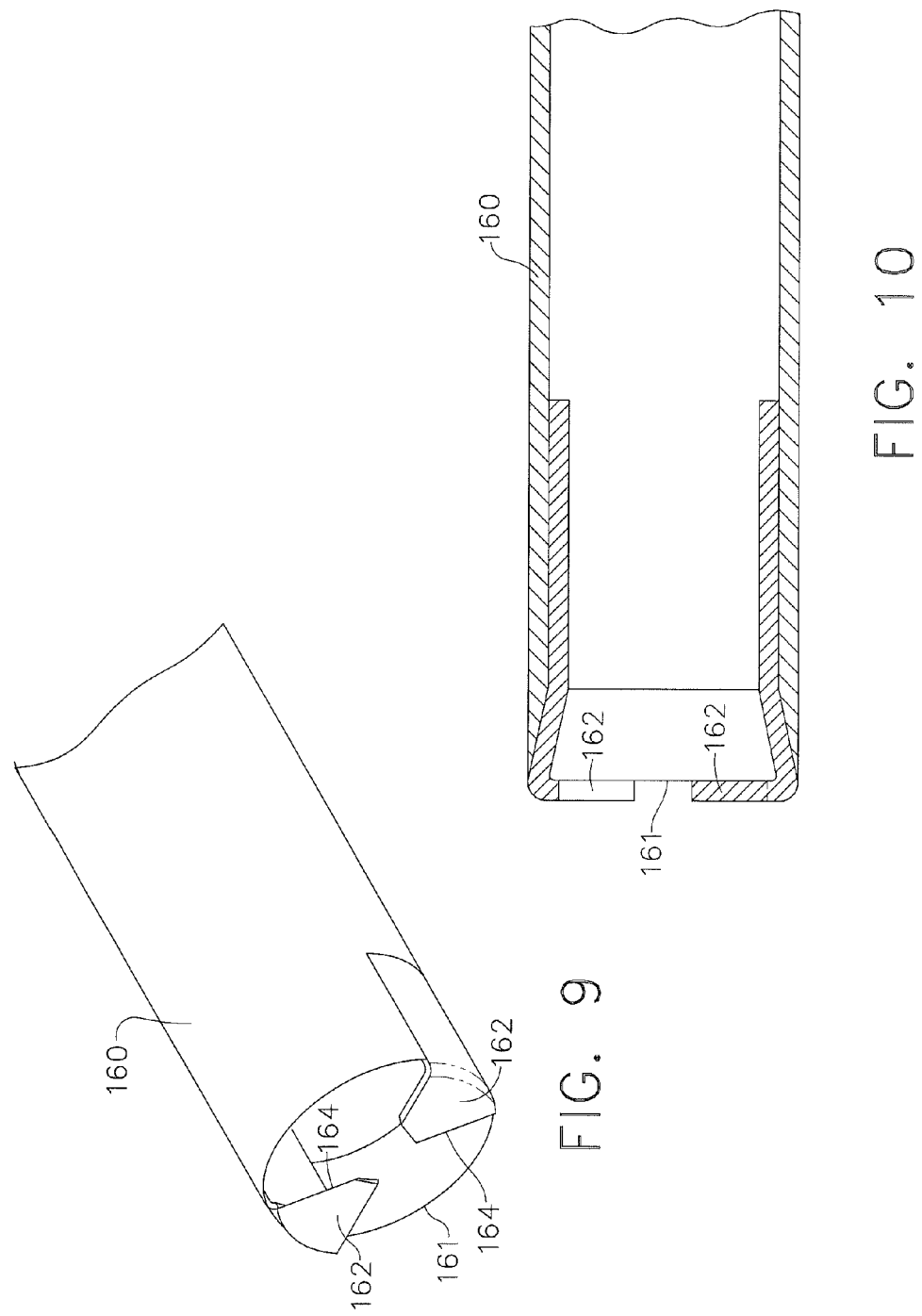

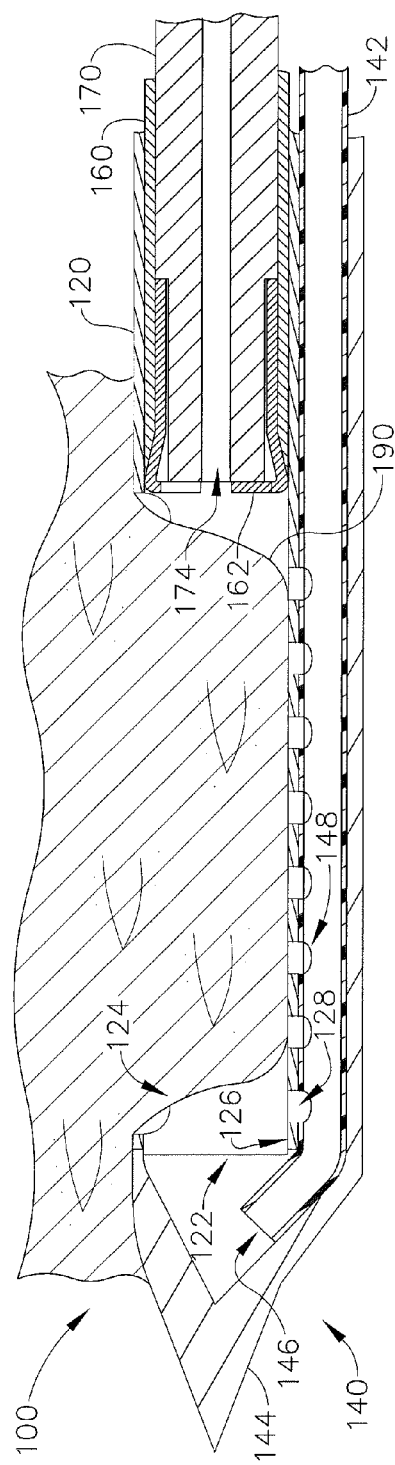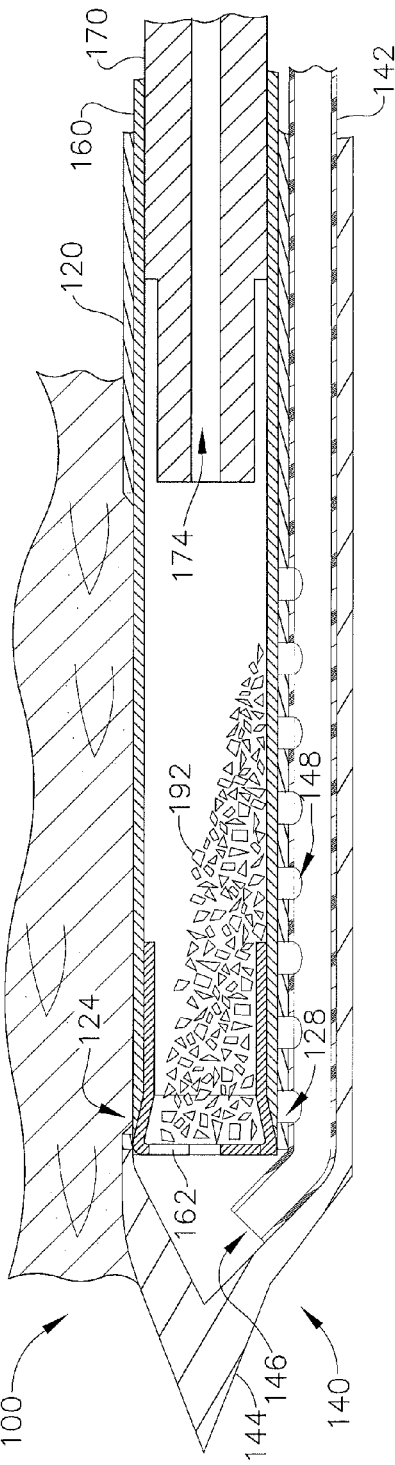

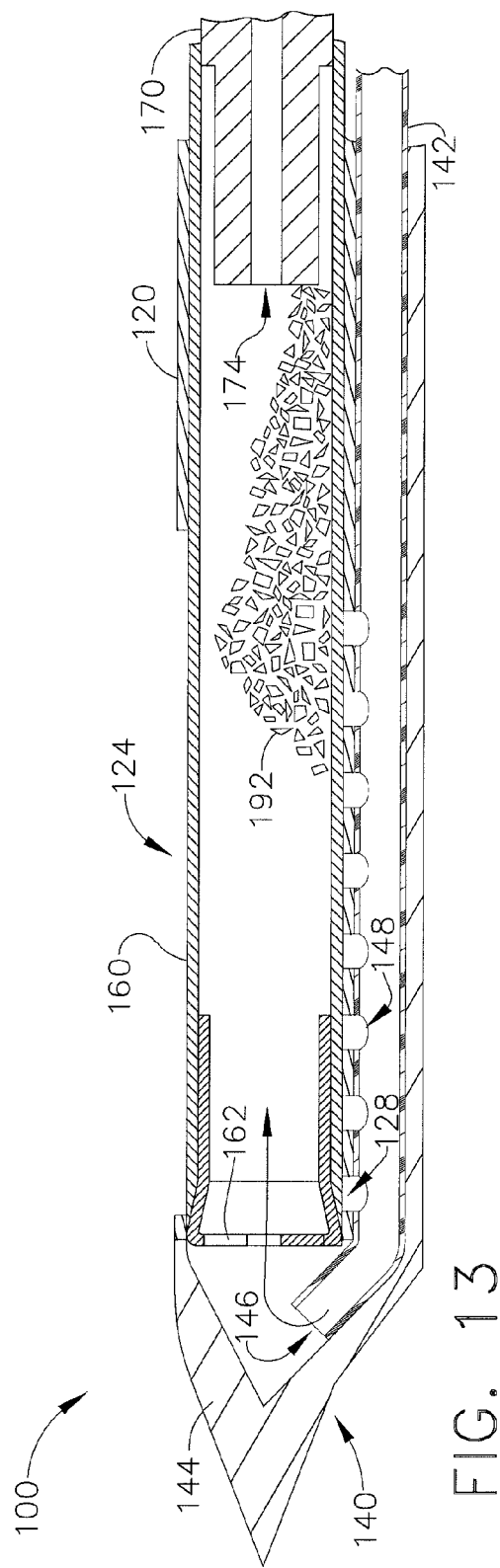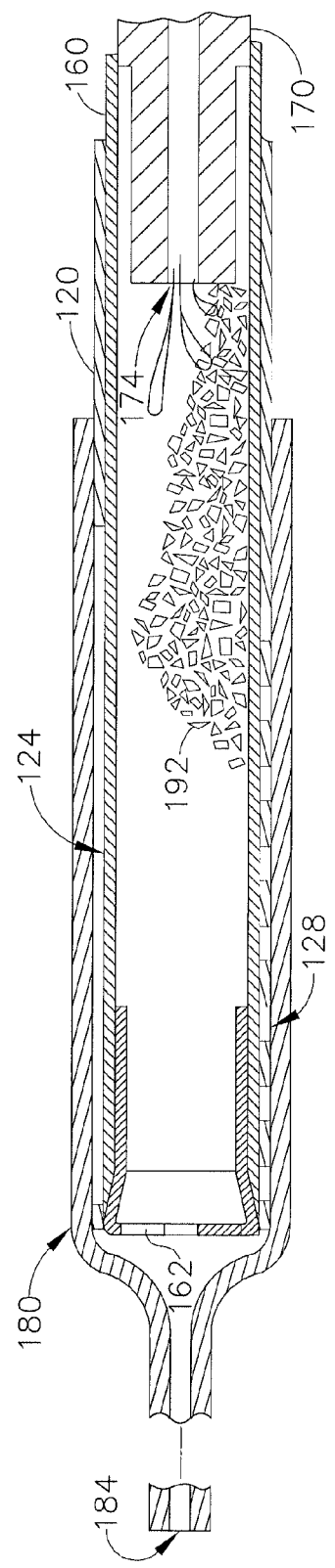

INSTRUMENT FOR APPLYING THERAPEUTIC CELLS, WITH DISTAL PORTION FOR PROCESSING THERAPEUTIC CELLS

BACKGROUND

Promoting and improving tissue healing is an important aspect of some medical treatments and procedures. For instance, promoting and improving tissue healing may lead to quicker recovery times and lessen the opportunity for infection, particularly in a post-surgical context. Some advancements in the medical arts pertaining to systems, methods, and devices to promote and improve tissue healing in patients aim to add active biological components (e.g., tissue particles, stem cells, other types of cells, etc.) to a wound site (e.g., surgical site, accidental trauma site, etc.) or other defect site (e.g., caused by disease or other condition, etc.) to promote tissue regeneration or accelerate tissue healing. When adding biological components to a site, such components may be added independently or as part of a specifically designed matrix or other mixture depending on the condition being treated and goals of the treatment. Some examples of cell-based therapy technology are disclosed in U.S. Pub. No. 2008/0311219, entitled "Tissue Fragment Compositions for the Treatment of Incontinence," published Dec. 18, 2008, the disclosure of which is incorporated by reference herein. Additional examples of cell-based therapy technology are disclosed in U.S. Pub. No. 2004/0078090, entitled "Biocompatible Scaffolds with Tissue Fragments," published Apr. 22, 2004, the disclosure of which is incorporated by reference herein. Additional examples of cell-based therapy technology are disclosed in U.S. Pub. No. 2008/0071385, entitled "Conformable Tissue Repair Implant Capable of Injection Delivery," published Mar. 20, 2008, now U.S. Pat. No. 7,875,296, issued Jan. 25, 2011, the disclosure of which is incorporated by reference herein.

Regardless of how the active biological components are delivered or applied to a site, the biological components must first be obtained and prepared. One approach for obtaining such biological components is to harvest the desired components from a healthy tissue specimen (e.g., in an adult human). Examples of devices and associated methods for collecting and processing harvested tissue are disclosed in U.S. Pub. No. 2004/0193071, entitled "Tissue Collection Device and Methods," published Sep. 30, 2004, now U.S. Pat. No. 7,794,408, issued Sep. 14, 2010, the disclosure of which is incorporated by reference herein. Additional examples of devices and associated methods for collecting and processing harvested tissue are disclosed in U.S. Pub. No. 2005/0038520, entitled "Method and Apparatus for Resurfacing an Articular Surface," published Feb. 17, 2005, the disclosure of which is incorporated by reference herein. Additional examples of devices and associated methods for collecting and processing harvested tissue are disclosed in U.S. Pat. No. 7,611,473, entitled "Tissue Extraction and Maceration Device," issued Nov. 3, 2009, the disclosure of which is incorporated by reference herein. Additional examples of devices and associated methods for collecting and processing harvested tissue are disclosed in U.S. Pub. No. 2008/0234715, entitled "Tissue Extraction and Collection Device," published Sep. 25, 2008, now U.S. Pat. No. 8,034,003, issued Oct. 11, 2011, the disclosure of which is incorporated by reference herein. Additional examples of devices and associated methods for processing harvested tissue are disclosed in U.S. Pub. No. 2005/0125077, entitled "Viable Tissue Repair Implants and Methods of Use," published Jun. 9, 2005, now U.S. Pat. No. 7,901,461, issued Mar. 8, 2011, the disclosure of which is incorporated by reference herein. Additional examples of devices and associated methods for collecting and processing harvested tissue are disclosed in U.S. Pat. No. 5,694,951, entitled "Method for Tissue Removal and Transplantation," issued Dec. 9, 1997, the disclosure of which is incorporated by reference herein. Additional examples of devices and associated methods for collecting and processing harvested tissue are disclosed in U.S. Pat. No. 6,990,982, entitled "Method for Harvesting and Processing Cells from Tissue Fragments," issued Jan. 31, 2006, the disclosure of which is incorporated by reference herein. Additional examples of devices and associated methods for collecting and processing harvested tissue are disclosed in U.S. Pat. No. 7,115,100, entitled "Tissue Biopsy and Processing Device," issued Oct. 3, 2006, the disclosure of which is incorporated by reference herein.

Once harvested and suitably processed (e.g., incorporated with a scaffold, etc.), biological material such as tissue fragments may be applied to a wound site or other type of site within the human body in a variety of ways. Various methods and devices for applying such biological material are disclosed in one or more of the U.S. patent references cited above. Additional methods and devices for applying such biological material are disclosed in U.S. Pub. No. 2005/0113736, entitled "Arthroscopic Tissue Scaffold Delivery Device," published May 26, 2005, now U.S. Pat. No. 8,673,021, issued Mar. 18, 2014, the disclosure of which is incorporated by reference herein.

While a variety of devices and techniques may exist for harvesting, processing, and applying biological components from a tissue specimen, it is believed that no one prior to the inventor(s) has made or used an invention as described herein.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings. In the drawings, like numerals represent like elements throughout the several views.

FIG. 6 depicts a partial, side cross-sectional view of the needle portion of FIG. 2 coupled with the adapter tip of FIG. 5 to form an adapted needle assembly, with the mincer and plunger each in the proximal position.

FIG. 7 depicts a partial, side cross-sectional view of the adapted needle assembly of FIG. 6, with fluid being introduced within the needle to mix with the minced tissue.

FIG. 8 depicts a partial, side cross-sectional view of the adapted needle assembly of FIG. 6, with the mincer and plunger both moved from the proximal position to the distal position to expel the tissue-fluid mixture through the adapter tip.

FIG. 9 depicts a partial end view of an exemplary tissue harvesting and mincing blade member.

FIG. 10 depicts a partial, side cross-sectional view of the blade member of FIG. 9.

FIG. 11 depicts a partial, side cross-sectional view of a needle adapter of a tissue harvesting and mincing system coupled with the blade member of FIG. 9 to produce a harvesting needle assembly, with the blade member in a proximal position and with a plunger in a proximal position.

FIG. 12 depicts a partial, side cross-sectional view of the harvesting needle assembly of FIG. 11, with the blade member moved from the proximal position to the distal position to mince tissue, and with the plunger remaining in the proximal position.

FIG. 13 depicts a partial, side cross-sectional view of the harvesting needle assembly of FIG. 11, with the blade member in the distal position and with the plunger remaining in the proximal position, with fluid being communicated to the interior of the blade member.

FIG. 14 depicts a partial, side cross-sectional view of the harvesting needle assembly of FIG. 11, with an exemplary fluid applier adapter tip coupled with the cannula.

Figure 1:
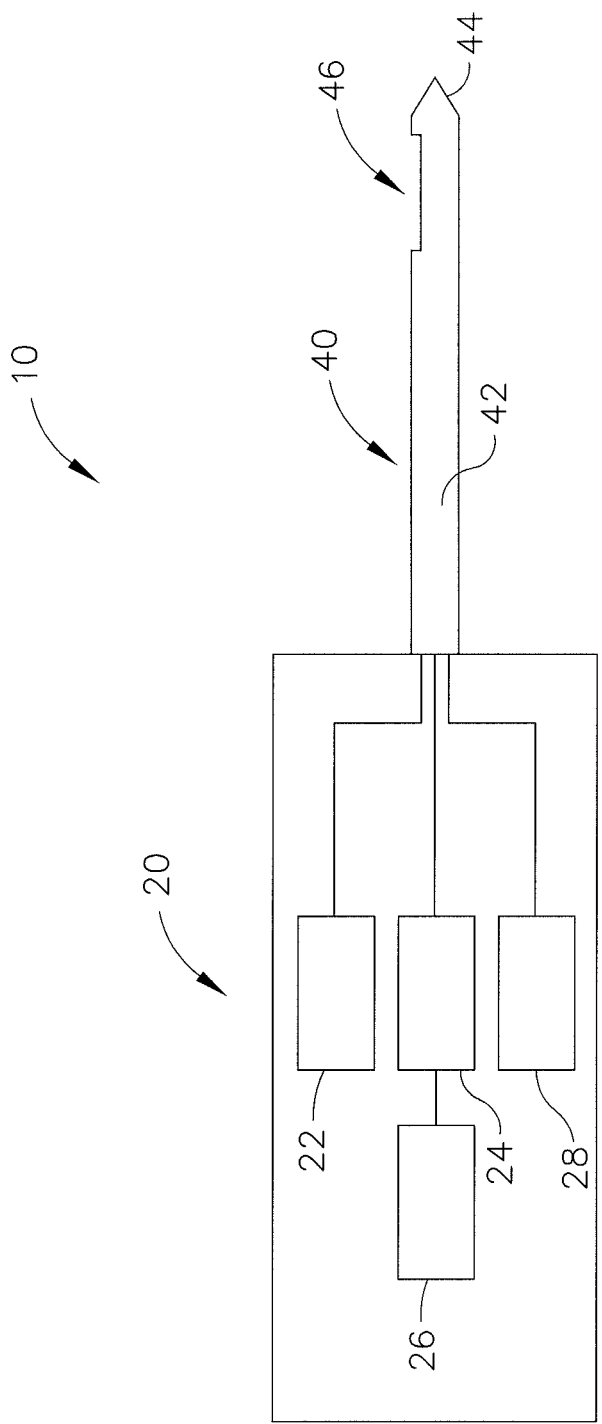
FIG. 1 depicts a system schematic view of an exemplary tissue harvesting and mincing system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples should not be used to limit the scope of the present invention. Other features, aspects, and advantages of the versions disclosed herein will become apparent to those skilled in the art from the following description, which is by way of illustration, one of the best modes contemplated for carrying out the invention. As will be realized, the versions described herein are capable of other different and obvious aspects, all without departing from the invention. Accordingly, the drawings and descriptions should be regarded as illustrative in nature and not restrictive.

I. Overview of Exemplary Treatment Compositions, Devices, and Methods

Examples described herein include devices that are operable to harvest tissue, mince or morcellate tissue, mix tissue particles with other medical fluid components, and/or dispense a medical fluid at a target site in a patient. As described in greater detail below, the medical fluid may include any of a variety of biocompatible materials that accelerate tissue healing, promote tissue regeneration, and/or provide other results. As used herein, the terms "tissue treatment composition," "tissue repair composition," and "medical fluid" should be read interchangeably. It should also be understood that a tissue treatment composition or medical fluid as referred to herein may have any suitable consistency, including but not limited to the consistency of a slurry.

A medical fluid as referred to herein may be derived from any biocompatible material, including but not limited to synthetic or natural polymers. The consistency of the medical fluid may be viscous, or gel-like, that of a slurry composed of microparticles, or any other suitable consistency. By way of example only, any fluid consistency that may permit injection through a catheter may be used. The medical fluid may also provide adhesive characteristics, such that once it is injected at a target site (e.g., into a fistula), the fluid coagulates or gels (e.g., allowing for a plug to be retained within a fistula). The medical fluid of the present example is also able to support cell migration and proliferation such that healing at a target site in a patient can occur. The fluid is suitable to be mixed with biological materials. Examples of medical fluid components include but are not limited to thrombin, platelet poor plasma (PPP) platelet rich plasma (PRP), starch, chitosan, alginate, fibrin, polysaccharide, cellulose, collagen, gelatin-resorcin-formalin adhesive, oxidized cellulose, mussel-based adhesive, poly (amino acid), agarose, amylose, hyaluronan, polyhydroxybutyrate (PHB), hyaluronic acid, poly(vinyl pyrrolidone) (PVP), poly(vinyl alcohol) (PVA), polylactide (PLA), polyglycolide (PGA), polycaprolactone (PCL), and their copolymers, VICRYL® (Ethicon, Inc., Somerville, N.J.), MONOCRYL material, PANACRYL (Ethicon, Inc., Somerville, N.J.), and/or any other material suitable to be mixed with biological material and introduced to a wound or defect site, including combinations of materials. Other suitable compounds, materials, substances, etc., that may be used in a medical fluid will be apparent to those of ordinary skill in the art in view of the teachings herein.

By way of example only, one or more components in a medical fluid or tissue treatment composition may comprise at least one viable tissue fragment having one or more viable cells that, once applied, can proliferate and integrate with tissue at a target site in a patient. For instance, viable cells may migrate out of a tissue particle and populate a scaffold material, which may be positioned at a target site in a patient. Such tissue fragments may have been harvested from the same patient in whom they are reapplied; or may have been harvested from another person or source. The tissue fragments may comprise autogenic tissue, allogenic tissue, xenogenic tissue, mixtures of any of the foregoing, and/or any other type(s) of tissue. The tissue fragments may include, for example, one or more of the following tissues or tissue components: stem cells, cartilage tissue, meniscal tissue, ligament tissue, tendon tissue, skin tissue, muscle tissue (e.g., from the patient's thigh, etc.), periosteal tissue, pericardial tissue, synovial tissue, fat tissue, bone marrow, bladder tissue, umbilical tissue, embryonic tissue, vascular tissue, blood and combinations thereof. Of course, any other suitable type of tissue may be used, including any suitable combination of tissue types. In some versions, the type of tissue used is selected from a tissue type most resembling the tissue at, near, or surrounding the target site (e.g., fistula, etc.).

Tissue for providing at least one viable tissue fragment may be obtained using any of a variety of tissue biopsy devices or using other types of tissue harvesting devices or techniques. Exemplary biopsy devices include those taught in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2007/0118048, entitled "Remote Thumbwheel for a Surgical Biopsy Device," published May 24, 2007, now U.S. Pat. No. 7,442,171, issued Oct. 28, 2008; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, now U.S. Pub. No. 2010/0160819, published Jun. 24, 2010 and now abandoned; and U.S. Non-Provisional patent application Ser. No. 12/483,305, entitled "Tetherless Biopsy Device with Reusable Portion," filed Jun. 12, 2009, now U.S. Pat. No. 8,206,316, issued Jun. 6, 2012. The disclosure of each of the above-cited U.S. patents, U.S. patent application Publications, and U.S. Non-Provisional patent applications is incorporated by reference herein. Such biopsy devices may be used to extract a plurality of tissue specimens from one or more sites in a single patient. It should also be understood that any suitable device described in any other reference that is cited herein may be used to harvest tissue. Additional examples of devices that may be used to harvest tissue will be described in greater detail below. Other examples will be apparent to those of ordinary skill in the art in view of the teachings herein. Tissue harvesting sites may include the same sites in which tissue is reapplied as part of a treatment. In addition or in the alternative, tissue may be harvested from one site and then reapplied at some other site as part of a treatment. In some versions, the tissue is reapplied in the same patient from whom the tissue was originally harvested. In some other versions, the tissue is applied in a patient who is different from the patient from whom the tissue was originally harvested.

A tissue specimen may be obtained under aseptic conditions, and then processed under sterile conditions to create a suspension having at least one minced, or finely divided, tissue fragment. In other words, harvested tissue may be diced, minced or morcellated, and/or otherwise processed. Harvested tissue specimens may be minced and otherwise processed in any of a variety of ways. For instance, examples of tissue mincing and processing are described in U.S. Pub. No. 2004/0078090, the disclosure of which is incorporated by reference herein. Alternatively, merely exemplary non-conventional devices and techniques that may be used to mince and process tissue will be described in greater detail below, while other examples will be apparent to those of ordinary skill in the art in view of the teachings herein. In order to ensure viability of the tissue, agitators or other features of a mincing and/or mixing device may be designed to sever and mix (rather than crush or compress) the tissue. In some settings, tissue specimens may be minced and/or mixed in a standard cell culture medium, either in the presence or absence of serum. Tissue fragments may also be contacted with a matrix-digesting enzyme to facilitate cell migration out of an extracellular matrix surrounding the cells. Suitable matrix-digesting enzymes that may be used in some settings include, but are not limited to, collagenase, chondroitinase, trypsin, elastase, hyaluronidase, peptidase, thermolysin, and protease. The size of each tissue fragment may vary depending on the target location, method for delivering the treatment composition to the target site, and/or based on various other considerations. For example, the tissue fragment size may be chosen to enhance the ability of regenerative cells (e.g., fibroblasts) in the tissue fragments to migrate out of the tissue fragments, and/or to limit or prevent the destruction of cell integrity. In some settings, ideal tissue fragments are between approximately 200 microns and approximately 500 microns in size. As another merely illustrative example, ideal tissue fragments may be sized within the range of approximately 0.05 $mm^3$ and approximately 2 $mm^3$; or more particularly between approximately 0.05 $mm^3$ and approximately 1 $mm^3$. Of course, various other tissue fragment sizes may be ideal in various different settings.

In some versions, a medical fluid may comprise minced tissue fragments suspended in a biocompatible carrier. Suitable carriers may include, for example, a physiological buffer solution, a flowable gel solution, saline, and water. In the case of gel solutions, the tissue repair composition may be in a flowable gel form prior to delivery at the target site, or may form a gel and remain in place after delivery at the target site. Flowable gel solutions may comprise one or more gelling materials with or without added water, saline, or a physiological buffer solution. Suitable gelling materials include biological and synthetic materials. Exemplary gelling materials include the following: proteins such as collagen, collagen gel, elastin, thrombin, fibronectin, gelatin, fibrin, tropoelastin, polypeptides, laminin, proteoglycans, fibrin glue, fibrin clot, platelet rich plasma (PRP) clot, platelet poor plasma (PPP) clot, self-assembling peptide hydrogels, Matrigel or atelocollagen; polysaccharides such as pectin, cellulose, oxidized regenerated cellulose, chitin, chitosan, agarose, or hyaluronic acid; polynucleotides such as ribonucleic acids or deoxyribonucleic acids; other materials such as alginate, cross-linked alginate, poly(N-isopropylacrylamide), poly(oxyalkylene), copolymers of poly(ethylene oxide)-poly(propylene oxide), poly(vinyl alcohol), polyacrylate, or monostearoyl glycerol co-Succinate/polyethylene glycol (MGSA/PEG) copolymers; and combinations of any of the foregoing. In addition to providing a flowable carrier solution for tissue fragments, a gelling agent(s) may also act as an adhesive that anchors the tissue repair composition at the target site. In some versions, an additional adhesive anchoring agent may be included in the tissue repair composition or medical fluid. Also, one or more cross-linking agents may be used in conjunction with one or more gelling agents in order to cross-link the gelling agent.

The concentration of tissue fragments in a carrier and/or one or more medical fluid components may vary depending on the target site location, method for delivering the treatment composition to the target site, and/or for various other reasons. By way of example, the ratio of tissue fragments to carrier (by volume) may be in the range of about 2:1 to about 6:1, or in the range of about 2:1 to about 3:1. The medical fluid may also include one more additional healing agents, such as biological components that accelerate healing and/or tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Similarly, in some versions where a scaffold plug is used in conjunction with a tissue repair composition, one or more of these additional biological components or additional treatment components may be provided on and/or within the scaffold plug. Some examples described herein may also include one or more adhesive agents in conjunction with viable tissue fragments.

As noted above, the harvested tissue may be combined with a scaffold material and/or other substances as part of a medical fluid, as described herein, for administration to the patient. To the extent that tissue is incorporated with a scaffold material, it should be understood that any suitable material or combination of materials may be used to provide a scaffold. By way of example only, scaffold material may include a natural material, a synthetic material, a bioabsorbable polymer, a non-woven polymer, other types of polymers, and/or other types of materials or combinations of materials. Examples of suitable biocompatible materials include starch, chitosan, cellulose, agarose, amylose, lignin, hyaluronan, alginate, hyaluronic acid, fibrin glue, fibrin clot, collagen gel, gelatin-resorcin-formalin adhesive, platelet rich plasma (PRP) gel, platelet poor plasma (PPP) gel, Matrigel, Monostearoyl Glycerol co-Succinate (MGSA), Monostearoyl Glycerol co-Succinate/polyethylene glycol (MGSA/PEG) copolymers, laminin, elastin, proteoglycans, polyhydroxybutyrate (PHB), poly(vinyl pyrrolidone) (PVP), polylactide (PLA), polyglycolide (PGA), polycaprolactone (PCL), and their copolymers, non-woven VICRYL® (Ethicon, Inc., Somerville, N.J.), MONOCRYL material, fibrin, non-woven poly-L-lactide, and non-woven PANACRYL (Ethicon, Inc., Somerville, N.J.). Polymers may include aliphatic polyesters, poly(amino acids), copoly(ether-esters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, poly(propylene fumarate), polyurethane, poly(ester urethane), poly (ether urethane), and blends and copolymers thereof. Suitable synthetic polymers for use in examples described herein may also include biosynthetic polymers based on sequences found in collagen, laminin, glycosaminoglycans, elastin, thrombin, fibronectin, starches, poly(amino acid), gelatin, alginate, pectin, fibrin, oxidized cellulose, chitin, chitosan, tropoelastin, hyaluronic acid, silk, ribonucleic acids, deoxyribonucleic acids, polypeptides, proteins, polysaccharides, polynucleotides, and combinations thereof. Other suitable materials or combinations of materials that may be used will be apparent to those of ordinary skill in the art in view of the teachings herein. It should also be understood that tissue mixed with a scaffold material may have any suitable particle size, and that the resulting mixture may at least initially have the consistency of a slurry or have any other suitable consistency. In some versions, the tissue particles include an effective amount of viable cells that can migrate out of the tissue particle and populate the scaffold. The term "viable," as used herein, should be understood to include a tissue sample having one or more viable cells.

In some versions, one or more components in a medical fluid or tissue treatment composition comprise one or more healing agents that promote tissue regeneration at a target site (e.g., within a fistula) and/or accelerate tissue healing at the target site. Healing agents may include any of a variety of biocompatible materials that accelerate tissue healing and/or promote tissue regeneration. Such biological components may include, for example, growth factors, proteins, peptides, antibodies, enzymes, platelets, glycoproteins, hormones, cytokines, glycosaminoglycans, nucleic acids, analgesics, viruses, isolated cells, or combinations thereof. The medical fluid may further include one or more additional treatment components that prevent infection, reduce inflammation, prevent or minimize adhesion formation, and/or suppress the immune system. In some versions where a scaffold is used in conjunction with a tissue treatment composition, one or more of these additional biological components or additional treatment components may be provided on and/or within the scaffold. Some examples described herein may also include one or more adhesive agents in conjunction with viable tissue fragments.

As used herein, the term "fluid communication" (or in some contexts "communication") means that there is a path or route through which fluid (gas, liquid or other flowable material) may flow between two components, either directly or through one or more intermediate components. Similarly, the term "conduit" encompasses a conduit within or integrated with a valve. In other words, fluid communication between two components means that fluid can flow from one component to another but does not exclude an intermediate component (e.g., a valve, etc.) between the two recited components that are in fluid communication. Similarly, two or more components may be in mechanical "communication" with each other even if intermediate components are interposed between those two or more components.

II. Exemplary Tissue Harvesting and Mincing Device Having Applier Adapter Tip

As shown in FIGS. 1-8, an exemplary tissue harvesting and mincing device (10) comprises a body portion (20) and a needle portion (40), which extends distally from body portion (20). Body portion (20) is configured to be handheld in the present example, and is fully operable by a single hand of the user such that the user's other hand is free to perform other tasks. Alternatively, body portion (20) may have any other suitable size or configuration, and may be manipulated in any other suitable way. In the present example, body portion (20) contains an actuation mechanism (22), a fluid pressure pump (24), a fluid reservoir (26), and a vacuum pump (28). Each of these components will be described in greater detail below. While these components are provided in body portion (20) in the present example, it should be understood that any or all of these components, or even just portions of one or more of these components, may be provided external to body portion (20) if desired.

Needle (40) of the present example comprises an elongate cannula (42) having a distal tip (44). Distal tip (44) is closed and is configured to pierce and penetrate tissue in the present example, though it should be understood that distal tip (44) may alternatively have various other configurations (e.g., blunt, open, etc.). A transverse aperture (46) is formed in cannula (42), proximal to tip (44). Transverse aperture (46) is configured to receive prolapsed tissue for harvesting as will be described in greater detail below. As best seen in FIGS. 2-4 and 6-8, cannula (42) also includes a first lumen (50) and a second lumen (52). Lumens (50, 52) run parallel to each other along the length of cannula (42) and are separated by a wall (54). Wall (54) defines a plurality of openings (56), which provide fluid communication between lumens (50, 52). In the present example, openings (56) are positioned along a longitudinal length that is approximately equal to and co-located with the longitudinal length along which transverse aperture (46) extends. It should be understood, however, that openings (56) may be positioned along and extend to any other suitable length.

A mincer (60) is provided in first lumen (50). Mincer (60) has a disc shape and includes a plurality of openings (62). Openings (62) are configured to mince tissue as will be described in further detail below. Mincer (60) is coupled with the distal end of a shaft (64), which is operable to drive mincer (60) within first lumen (50). In particular, the proximal end of shaft (64) is coupled with actuation mechanism (22). When activated, actuation mechanism (22) is operable to translate shaft (64) distally and proximally along the longitudinal axis defined by shaft (64), to provide corresponding translation of mincer (60) within first lumen (50). In addition, actuation mechanism (22) is operable to rotate shaft (64) along the longitudinal axis defined by shaft (64), to provide corresponding rotation of mincer (60) within first lumen (50). In some versions, however, shaft (64) merely translates and does not also rotate. Other suitable configurations and operabilities of mincer (60) will be apparent to those of ordinary skill in the art in view of the teachings herein.

A plunger (70) is also provided in first lumen (50). Plunger (70) has a cylindraceous shape in the present example and defines a longitudinal bore through which shaft (64) coaxially extends. In particular, plunger (70) permits shaft (64) to rotate and translate within this bore, even as plunger (70) remains stationary relative to cannula (42). Plunger (70) is also coupled with actuation mechanism (22). When activated, actuation mechanism (22) is operable to translate plunger (70) distally and proximally along the longitudinal axis defined by plunger (70). It should also be understood that actuation mechanism (22) is operable to translate shaft (64) and plunger (70) independently of each other in the present example. Plunger (70) presents a distal face (72), which is configured to assist in pushing a medical fluid out from first lumen (50) through transverse aperture (46) as will be described in greater detail below.

Actuation mechanism (22) may comprise a variety of different kinds of components, such as a motorized device and/or a pneumatic device, including but not limited to a conventional DC motor, an AC motor, a pneumatic motor, a pneumatic linear actuator, an electromechanical linear actuator, a piezoelectric oscillator, an electroactive polymer actuator, an electromagnetic actuator, and/or a variety of other types of movement-inducing devices. In some versions, actuation mechanism (22) may be configured similar to a mechanism used in a conventional breast biopsy device to actuate a tubular cutter. For instance, actuation mechanism (22) may comprise a modified version of the cutter actuation mechanism (or components thereof) as taught in any of the following: U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; now U.S. Pat. No. 7,442,171, issued Oct. 28, 2008; U.S. Pub. No. 2008/0214955, entitled "Presentation of Biopsy Sample by Biopsy Device," published Sep. 4, 2008; U.S. Non-Provisional patent application Ser. No. 12/337,942, entitled "Biopsy Device with Central Thumbwheel," filed Dec. 18, 2008, now U.S. Pub. No. 2010/0160819, published Jun. 24, 2010 and now abandoned; and U.S. Non-Provisional patent application Ser. No. 12/483,305, entitled "Tetherless Biopsy Device with Reusable Portion," filed Jun. 12, 2009, now U.S. Pat. No. 8,206,316, issued Jun. 6, 2012. The disclosure of each of the above-cited U.S. patents, U.S. patent application Publications, and U.S. Non-Provisional patent applications is incorporated by reference herein. It should also be understood that actuation mechanism (22) may be manually operated, such as by a slider, crank, dial, or other type of manual actuator. Other suitable components and configurations for actuation mechanism (22) will be apparent to those of ordinary skill in the art in view of the teachings herein.

Fluid pressure pump (24) comprises a conventional pump that is in fluid communication with fluid reservoir (26) and second lumen (52). In some versions, fluid pressure pump (24) and actuation mechanism (22) are driven by the same motor or other source. In some versions, fluid pressure pump (24) comprises a manually operable syringe barrel and plunger, in which case fluid pressure pump (24) and fluid reservoir (26) may be integral with each other. Fluid reservoir (26) contains a portion of medical fluid. For instance, fluid reservoir (26) may contain one or more of the various fluid components mentioned above as being suitable in various formulations of medical fluid. Fluid pressure pump (24) is operable to drive fluid from fluid reservoir (26) distally through second lumen (52) as will be described in greater detail below. As previously noted, all or part of fluid pressure pump (26) and/or fluid reservoir (26) may be located external to body (20) in some versions. For instance, a flexible fluid conduit may couple second lumen (52) with an external fluid pressure pump (24) and/or fluid reservoir (26) in some versions. In addition, fluid reservoir (26) may be configured to receive one or more selected fluids provided by the user in some versions. For instance, fluid reservoir (26) may include an injection port with a self-sealing septum or some other type of port allowing a user to introduce one or more fluids into fluid reservoir (26) before use. In addition or in the alternative, fluid reservoir (26) may be provided with fluid already contained therein. As another merely illustrative example, fluid pressure pump (24) may be omitted altogether, and fluid reservoir (26) may be positioned higher than needle portion (40), such that fluid in fluid reservoir (26) is gravity-fed into second lumen (52).

Vacuum pump (28) comprises a conventional vacuum pump that is in fluid communication with second lumen (52).

Figure 2:
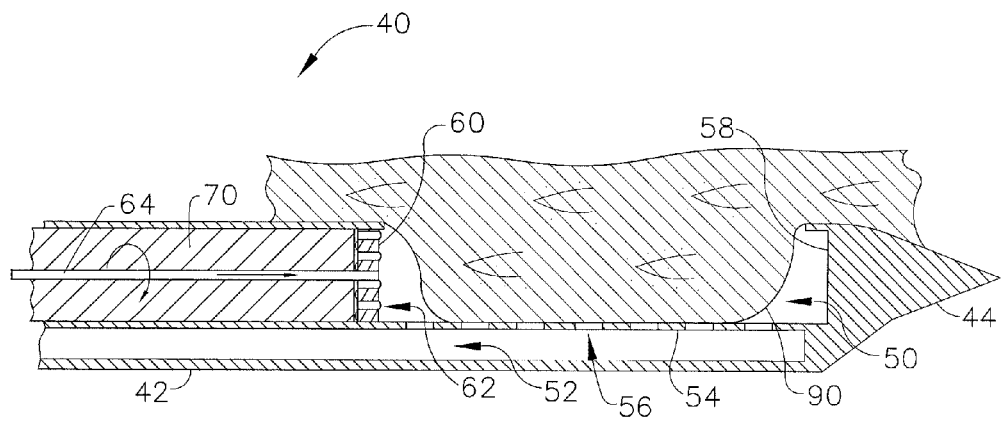
FIG. 2 depicts a partial, side cross-sectional view of a needle portion of the system of FIG. 1, with a mincer and plunger each in a proximal position to allow the prolapse of tissue into a side aperture of the needle.

In some versions, vacuum pump (28) and actuation mechanism (22) are driven by the same motor or other source. Vacuum pump (28) is operable to draw a vacuum through second lumen (52) to assist in the prolapse of tissue (90) through transverse aperture (46) as shown in FIG. 2. Such a vacuum may be communicated through openings (56). In some versions, openings (56) of wall (54) and openings of (62) mincer (60) are sized and configured such that tissue particles (92, 94) minced by mincer (60) will not be communicated to second lumen (52) via openings (56) when a vacuum is being drawn through second lumen (52). As previously noted, all or part of vacuum pump (28) may be located external to body (20) in some versions. For instance, a flexible fluid conduit may couple second lumen (52) with an external fluid vacuum pump (28) in some versions. It should also be understood that vacuum pump (28) may be completely omitted in some versions. For instance, tissue (90) may sufficiently prolapsed through aperture (46) on its own in some versions. In addition or in the alternative, a physician may rely on external palpation of the patient's tissue in order to facilitate sufficient prolapse of tissue (90) through aperture (46), such as by pressing on the patient's skin near the insertion site of needle portion (40), at the approximate location of aperture (46), etc.

Figure 5:
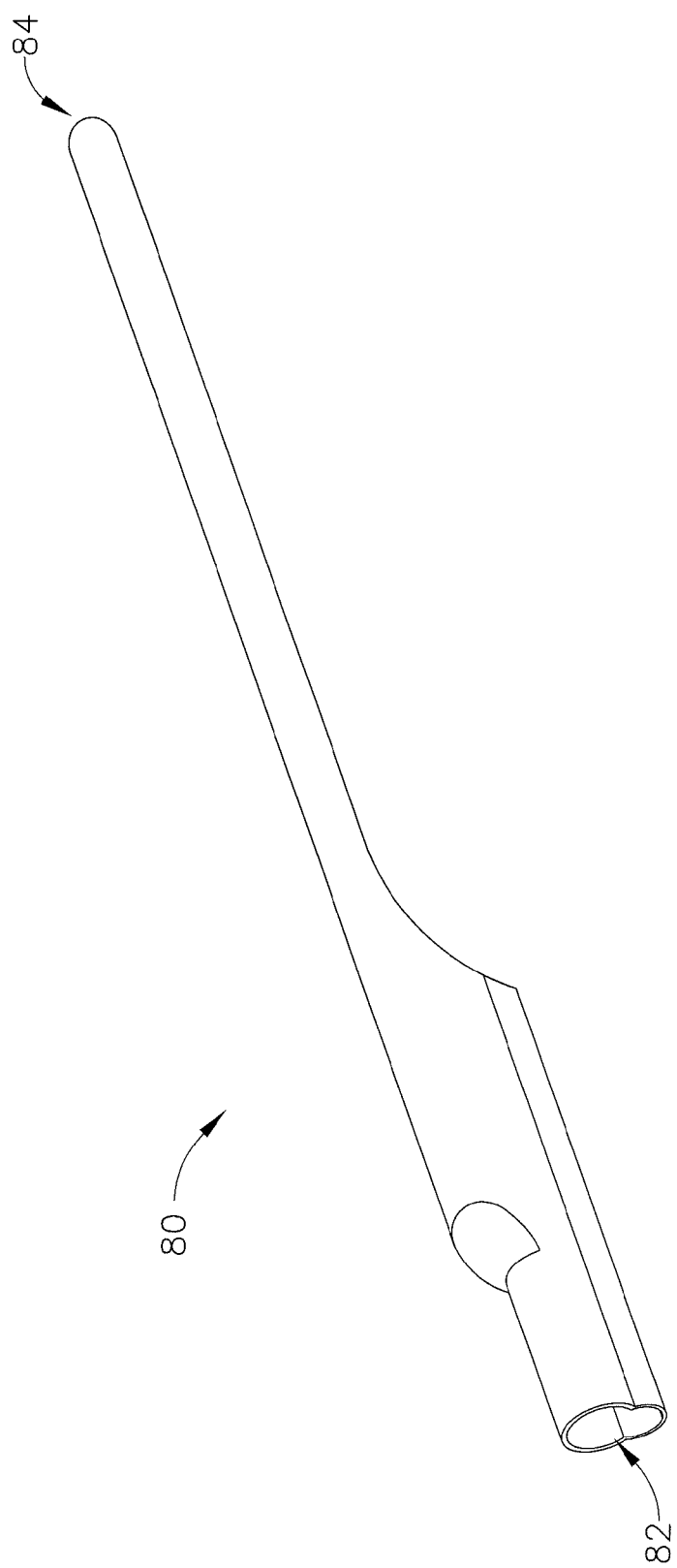
FIG. 5 depicts a perspective view of an exemplary medical fluid applier adapter tip.

Tissue harvesting and mincing device (10) of the present example also includes an applier adapter tip (80) as shown in FIG. 5. Adapter tip (80) includes a proximal opening (82) and a distal opening (84), with a lumen (86) providing open communication from proximal opening (82) to distal opening (84). As shown in FIGS. 6-8, adapter tip (80) is configured to fit over the distal end of needle portion (40). In particular, distal tip (44) of needle portion (40) may be inserted through proximal opening (82) of adapter tip (80) until distal tip (44) grounds out against a proximally facing sidewall surface (88) of adapter tip (80). As can also be seen in FIGS. 6-8, adapter tip (80) includes a protruding portion (89) that is positioned above transverse aperture (46) when adapter tip (80) is secured to needle portion (40). Protruding portion (89) allows fluid to be communicated from needle portion (40) through transverse aperture (46) and further through distal opening (84) as will be described in greater detail below. Adapter tip (80) may provide a substantially snug fit against needle portion (40). Adapter tip (80) may be flexible, semi-flexible, rigid, or have any other suitable properties.

Figure 3:
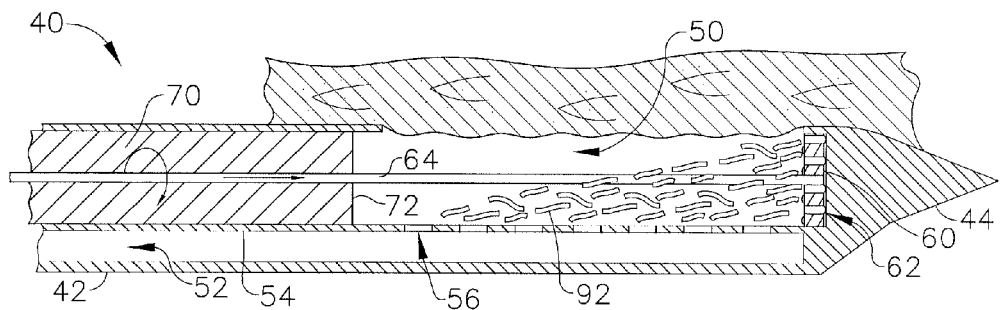
FIG. 3 depicts a partial, side cross-sectional view of the needle portion of FIG. 2, with the mincer moved from the proximal position to a distal position to mince tissue, and with the plunger remaining in the proximal position.
Figure 4:
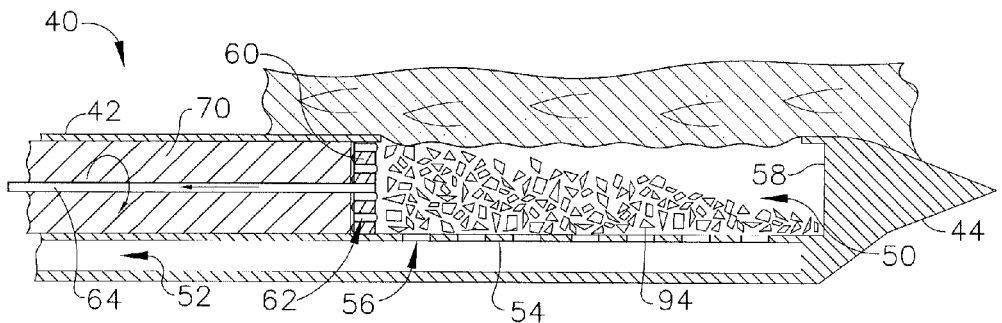
FIG. 4 depicts a partial, side cross-sectional view of the needle portion of FIG. 2, with the mincer moved from the distal position back to the proximal position to mince tissue further, and with the plunger remaining in the proximal position.

FIGS. 2-4 depict a first phase of an exemplary use of tissue harvesting and mincing device (10). Needle portion (40) is first inserted into a patient's tissue (e.g., thigh muscle, etc.). Tissue (90) is then prolapsed through transverse aperture (46) as shown in FIG. 2. Such prolapse of tissue may be facilitated through activation of vacuum pump (28) (if one is included), palpation, and/or otherwise. Next, actuation mechanism (22) advances mincer (60) distally while rotating mincer (60) about the longitudinal axis defined by shaft (64), as shown in FIG. 3. As mincer (60) advances, mincer (60) presses tissue (90) against face (58) of first lumen (50), which extrudes tissue (90) proximally through openings (62) to form elongate tissue particles (92). As noted above, to the extent that a vacuum pump (28) is included, vacuum pump (28) may remain active at this time to prevent mincer (60) from simply pushing tissue (90) back out through transverse aperture (46). In addition or in the alternative, the user may maintain external pressure on the patient's tissue to prevent mincer (60) from simply pushing tissue (90) back out through transverse aperture (46). After mincer (60) has reached face (58) of first lumen (50), actuation mechanism (22) retracts mincer (60) proximally to further mince tissue particles (92) into smaller tissue particles (94) as shown in FIG. 4. In particular, retraction of mincer (60) presses tissue particles (92) against face (72) of plunger (70), which extrudes tissue particles (92) distally through openings (62) to form smaller tissue particles (94). In some versions, mincer (60) may also be rotated about the longitudinal axis defined by shaft (64) during this retraction.

FIGS. 6-8 depict a second phase of an exemplary use of tissue harvesting and mincing device (10). In particular, needle portion (40) is withdrawn from the patient and adapter tip (80) is secured to needle portion (40) as shown in FIG. 6. Fluid pressure pump (24) is then activated to communicate a medical fluid component from fluid reservoir (26) into second lumen (52) as shown in FIG. 7. Such fluid passes through openings (56) into first lumen (50) to mix with tissue particles (94) as is also shown in FIG. 7. Mincer (60) and plunger (70) are then advanced distally to expel the mixture from first lumen (50) as shown in FIG. 8. In some versions, mincer (60) is advanced distally before plunger (70) and/or is reciprocated before plunger (70) is advanced in order to further mix tissue particles (94) with the liquid from fluid reservoir (26). With mincer (60) and plunger (70) both advanced distally as shown in FIG. 8, medical fluid (98) is expelled through distal opening (84) of adapter tip (80). Such medical fluid (98) may be administered at any suitable site within a patient, including but not limited to a surgical site, an accidental trauma site, an anatomical defect (e.g., fistula, etc.), and/or any other suitable type of site. In some other versions, medical fluid (98) is expelled directly through transverse aperture (46) at the target site, without adding adapter tip (80) to needle portion (40). Various other suitable ways in which tissue harvesting and mincing device (10) may be made and used will be apparent to those of ordinary skill in the art in view of the teachings herein.

III. Exemplary Tissue Harvesting and Mincing Device Having Hollow Cutter and Modular Tip Another exemplary tissue harvesting and mincing device (100) is shown in FIGS. 9-14. Tissue harvesting and mincing device (100) of this example includes a body portion (not shown) and a cannula (120) that extends distally from the body portion. The body portion may be configured similar to body portion (20) described above. Alternatively, the body portion may have any other suitable configuration. Cannula (120) has an open distal end (122), a transverse aperture (124) located proximal to open distal end (122), and a lower wall portion (126) that defines a plurality of openings (128). A mincer (160) is positioned within cannula (120). As best seen in FIGS. 9-10, mincer (160) of this example is tubular in shape and includes a sharpened distal edge (161) and a pair of inwardly directed blades (162) at its distal end. Each blade (162) has a respective cutting edge (164). An actuation mechanism (not shown) in the body of tissue harvesting and mincing device (100) is operable to reciprocate mincer (160) within cannula (120) and simultaneously rotate mincer (160) within cannula (120). The actuation mechanism may be configured similar to actuation mechanism (22) described above. Alternatively, the actuation mechanism may have any other suitable configuration. In some versions, the actuation mechanism provides manual translation and rotation of mincer (160). When mincer (160) is actuated, cutting edges (161, 164) of blades (162) are configured to mince tissue (190) into minced tissue particles (192).

A plunger (170) is coaxially disposed within mincer (160). Plunger (170) has a distal face (172) and defines a bore (174) along its longitudinal axis. The actuation mechanism is also operable to translate plunger (170) within cannula (120). In some versions, the actuation mechanism provides manual translation of plunger (170). Bore (174) of plunger (170) may be in fluid communication with a fluid pressure pump (not shown), a fluid reservoir (not shown), and/or a vacuum source (not shown) located within the body portion of tissue harvesting and mincing device (100) and/or located elsewhere.

As shown in FIGS. 11-13, cannula (120) is configured to receive a needle adapter tip (140). Needle adapter tip (140) extends along at least part of the length of cannula (120), and includes a conduit (142) that is positioned adjacent to lower wall portion (126) of cannula (120) when needle adapter tip (140) is secured to cannula (120). Conduit (142) includes a plurality of transverse openings (148) that align with openings (128) of cannula (120) and a distal opening (146) that is positioned distal to open distal end (122) of cannula (120). Like bore (174), conduit (142) may be in communication with a fluid pressure pump, a fluid reservoir, and/or a vacuum source located within the body portion of tissue harvesting and mincing device (100) and/or located elsewhere. Needle adapter tip (140) also has a closed distal tip (144) that is configured similar to distal tip (44) described above. Needle adapter tip (140) is configured to provide a snug fit with cannula (120).

As shown in FIG. 14, needle adapter tip (140) may be replaced with an applier adapter tip (180). Applier adapter tip (180) of this example is substantially similar in function to adapter tip (80) described above. Applier adapter tip (180) is configured to slide over a distal portion of cannula (120) with a snug fit. Applier adapter tip (180) thus substantially blocks off openings (128) of cannula (120) and transverse aperture (124) when applier adapter tip (180) is secured to cannula (120). Applier adapter tip (180) includes a distal opening (184) that communicates with the hollow interior of mincer (160). Applier adapter tip (180) may be flexible, semi-flexible, rigid, or have any other suitable properties.

FIGS. 11-14 depict an exemplary use of tissue harvesting and mincing device (100). At the initial stages of operation, needle adapter tip (140) is secured to cannula (120), and they are together inserted into a patient's tissue (e.g., thigh muscle, etc.). Tissue (190) is then prolapsed through transverse aperture (126) as shown in FIG. 11. Such prolapse of tissue may be facilitated through activation of a vacuum pump (if one is included), palpation, and/or otherwise. To the extent that a vacuum is used at this stage, such a vacuum may be communicated through bore (174) and/or through conduit (142). Next, the actuation mechanism advances mincer (160) distally while rotating mincer (160) about its longitudinal axis, as shown in FIG. 12. As mincer (160) advances, cutting edges (164) of blades (162) mince tissue (190) into tissue particles (192). Plunger (170) remains in a proximal position during this time. As noted above, to the extent that a vacuum pump is included, the vacuum pump may remain active at this time to prevent mincer (160) from simply pushing tissue (190) back out through transverse aperture (126). In addition or in the alternative, the user may maintain external pressure on the patient's tissue to prevent mincer (160) from simply pushing tissue (190) back out through transverse aperture (126).

After mincer (160) has reached a distal position, a pressurized medium is communicated through conduit (142) to urge minced tissue particles (192) proximally in mincer (160) as shown in FIG. 13. Such a pressurized medium may include pressurized air, a medical fluid component, and/or any other suitable kind(s) of medium. It should be understood that this stage may be carried out while cannula (120) and needle adapter tip (140) are still inserted in the patient or after cannula (120) and needle adapter tip (140) have been withdrawn from the patient. Once cannula (120) and needle adapter tip (140) have been withdrawn from the patient and minced tissue particles (192) have been urged proximally in mincer (160), needle adapter tip (140) is pulled off of cannula (120) and applier adapter tip (180) is secured to cannula (120) as shown in FIG. 14. During this process, mincer (160) remains in a distal position to effectively close off transverse aperture (124). A medical fluid component is then communicated distally through bore (174) to mix with minced tissue particles (192). A removable cap (not shown) may be provided at distal opening (184) of applier adapter tip (180) to prevent undesired leakage of medical fluid through distal opening (184). It should also be understood that mincer (160) may be reciprocated at this stage to further mix minced tissue particles (192) with the medical fluid component to provide a medical fluid mixture.

When the medical fluid mixture is to be administered to the patient, distal opening (184) is positioned at the target site, such as a surgical site, an accidental trauma site, an anatomical defect (e.g., fistula, etc.), and/or any other suitable type of site. In some versions, plunger (170) is advanced distally to urge the medical fluid mixture (including minced tissue particles (192), etc.) out through distal opening (184). In addition or in the alternative, a pressurized medium may be communicated through bore (174) to expel the medical fluid mixture out through distal opening (184). In some other versions, the medical fluid mixture is expelled directly through the open distal end of mincer (160) at the target site, without adding adapter tip (180) to cannula (120). Various other suitable ways in which tissue harvesting and mincing device (100) may be made and used will be apparent to those of ordinary skill in the art in view of the teachings herein.

IV. Exemplary Tissue Harvesting and Mincing Device Having Movable Mincing Die

FIGS. 15-18 depict yet another exemplary tissue harvesting and mincing device (200). Tissue harvesting and mincing device (200) of this example includes a body portion (220), a needle adapter (240), and an applier adapter (280). Body portion (220) includes a male port (222) that is configured to be selectively coupled with a female port (242) of needle adapter (240) or a female port (282) of applier adapter (280). Other components of body portion (220) will be described in greater detail below. Needle adapter (240) of this example includes a tubular cutter (244) that is slidably disposed within an outer needle (250). Cutter (244) includes a sharpened distal edge (246) and female port (242) at its proximal end. Outer needle (250) includes a closed distal tip (252), a transverse aperture (254), a conduit (256), and a proximal flange (258). Distal tip (252) has a configuration similar to that of distal tip (44) described above. Conduit (256) is configured similar to conduit (142) described above. A plurality of openings (260) provide fluid communication between conduit (256) and the lumen in which cutter (244) is disposed, similar to openings (148) described above. Of course, as with openings (148) described above, openings (260) may be omitted if desired.

A block (262) is secured to proximal flange (258) of needle (250), facilitating relative translation between needle (250) and cutter (244). For instance, with cutter (244) being held in a fixed position relative to a patient, a user may grip block (262) and slide it proximally/distally to translate needle (250) relative to cutter (244). Alternatively, a user may grip block (262) to hold needle (250) in a fixed position relative to a patient, then slide cutter (244) distally/proximally to translate cutter (244) relative to needle (250). It should be understood that relative translational movement between cutter (244) and needle (250) may effectively open and close transverse aperture (254). When the distal portion of needle adapter (240) is inserted in a patient, this relative motion may also cause distal edge (246) of cutter (244) to sever a tissue core (290), which will then be captured in the lumen (248) defined by cutter (244). While relative movement between cutter (244) and needle (250) is provided manually in the present example, it should be understood that such movement may alternatively be provided by an actuation mechanism using any suitable actuation components described herein and/or described in any reference cited herein.

Conduit (256) of the present example has a proximal end (257) that is suitable for coupling with a pressurized medium source (not shown). For instance, proximal end (257) of conduit (256) may be in communication with a pump, a charged air canister, a syringe, etc. The pressurized medium communicated through conduit (256) may comprise air, saline, a medical fluid component, and/or any other suitable type of medium. It should be understood that communication of a pressurized medium through conduit (256) will act on the distal face of tissue core (290), transporting tissue core (290) proximally through lumen (248) of cutter (244) toward body portion (220) as will be described in greater detail below. It should also be understood that a vacuum may be communicated through conduit (256) to assist in prolapsing tissue through transverse aperture (254) before tissue core (290) is severed from the patient and during the severing of tissue core (290) from the patient. Such a vacuum may be provided by a pump or syringe, etc., coupled with proximal end (257); and may be switched to a pressurized medium after tissue core (290) has been severed.

Body portion (220) of the present example comprises a housing (224), a piston (226), a valve (230), and a mincing die (234). Housing (224) of the present example is configured to be handheld, though it should be understood that any other suitable configuration may be used. Piston (226) of the present example comprises a head (227), a shaft (228), and an o-ring (229). O-ring (229) is configured to provide a seal around head (227) within housing (224). Head (227) and housing (224) together define a reservoir (221), which is configured to hold a medical fluid component (294). As will be described in greater detail below, shaft (228) may be pushed distally to reduce the effective capacity of reservoir (221), thereby expelling the contents of reservoir (221) out through port (222). Such distal advancement may be provided manually or by any suitable actuation mechanism as described elsewhere herein.

Figure 15:
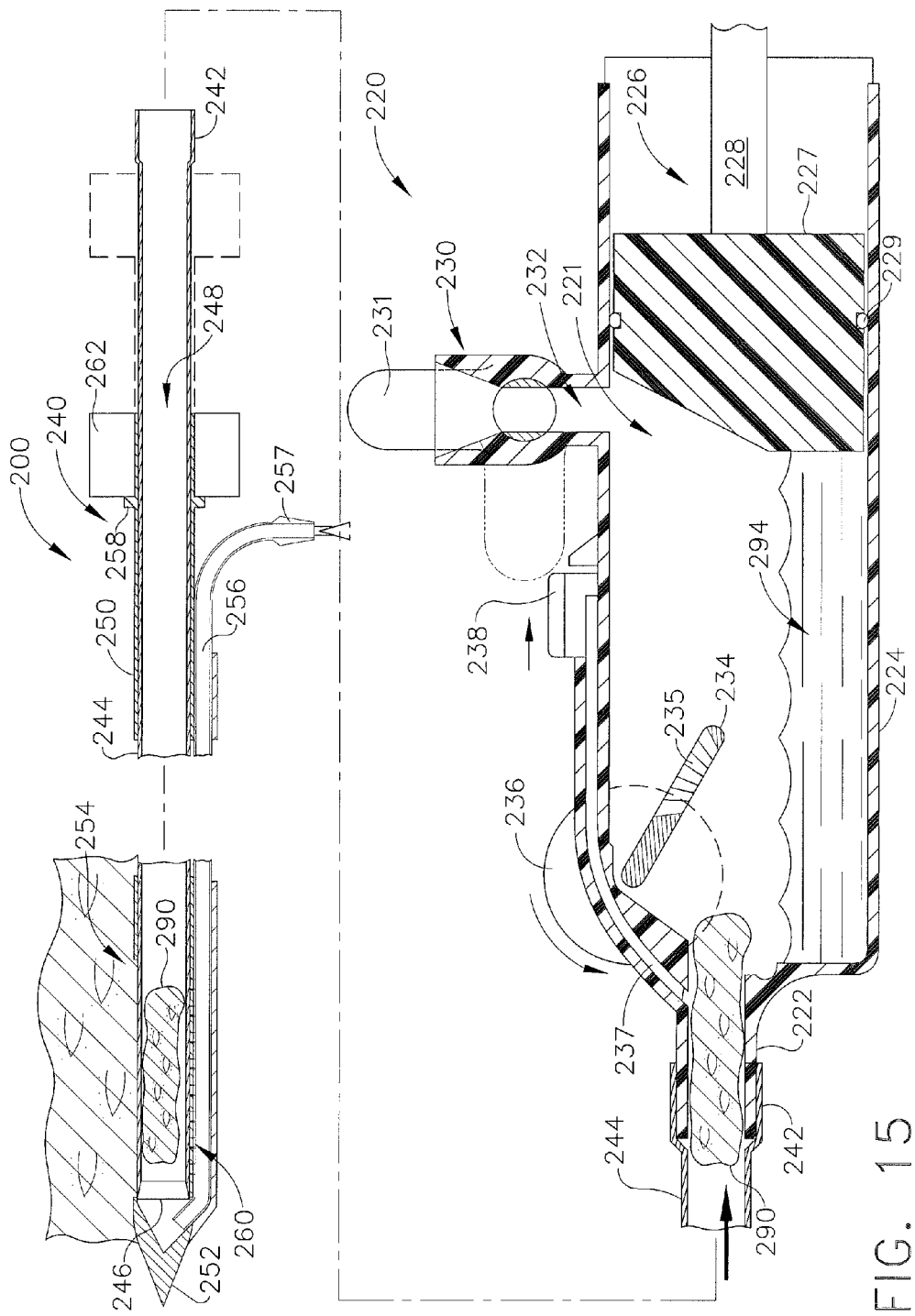
FIG. 15 depicts a side cross-sectional view of another exemplary tissue harvesting and mincing system, with a mincing die in a non-mincing position and with a tissue specimen entering a mixing chamber.

Valve (230) of the present example comprises a lever (231), which is operable to selectively open (FIGS. 15-16) and close off (FIGS. 17-18) a port (232). Port (232) is in fluid communication with reservoir (221), such that port (232) may be used to introduce a medical fluid component (294) to reservoir (221) as described in greater detail below. Mincing die (234) comprises a plurality of mincing blades (235) and a finger wheel (236) that is operable to rotate mincing die (234). In particular, finger wheel (236) is rotatable to selectively position mincing blades (235) between reservoir and port (222) (FIGS. 16-18) or away from port (222) (FIG. 15). Of course, various other suitable components or features may be used to selectively position mincing blades (235). As will be described in greater detail below, mincing blades (235) are configured to mince tissue core (290) into minced tissue particles (294) when tissue core (290) is forced through mincing blades (235).

Body portion (220) also includes a sliding gate (237), which is operable to selectively close off port (222) of body portion. In particular, gate (237) is movable between a first position (FIGS. 16-17) in which gate (237) blocks port (222); and a second position (FIGS. 15 and 18) in which gate (237) does not block port (222). A slider (238) is coupled with gate (237), and is manually operable to selectively transition gate (237) between the first and second positions. Of course, a variety of other components or features may be used in addition to or in lieu of slider (238). It should also be understood that a variety of other components or features may be used in addition to or in lieu of gate (237) to selectively close off port (222).

Applier adapter (280) of the present example comprises a female port (282) at its proximal end and an open distal end (283). Female port (282) may provide a substantially snug fit against port (222) of body portion (220). Applier adapter (280) may be flexible, semi-flexible, rigid, or have any other suitable properties. As will be described in greater detail below, applier adapter (280) may be used to administer a medical fluid (296) to a target site in a patient.

Figure 16:
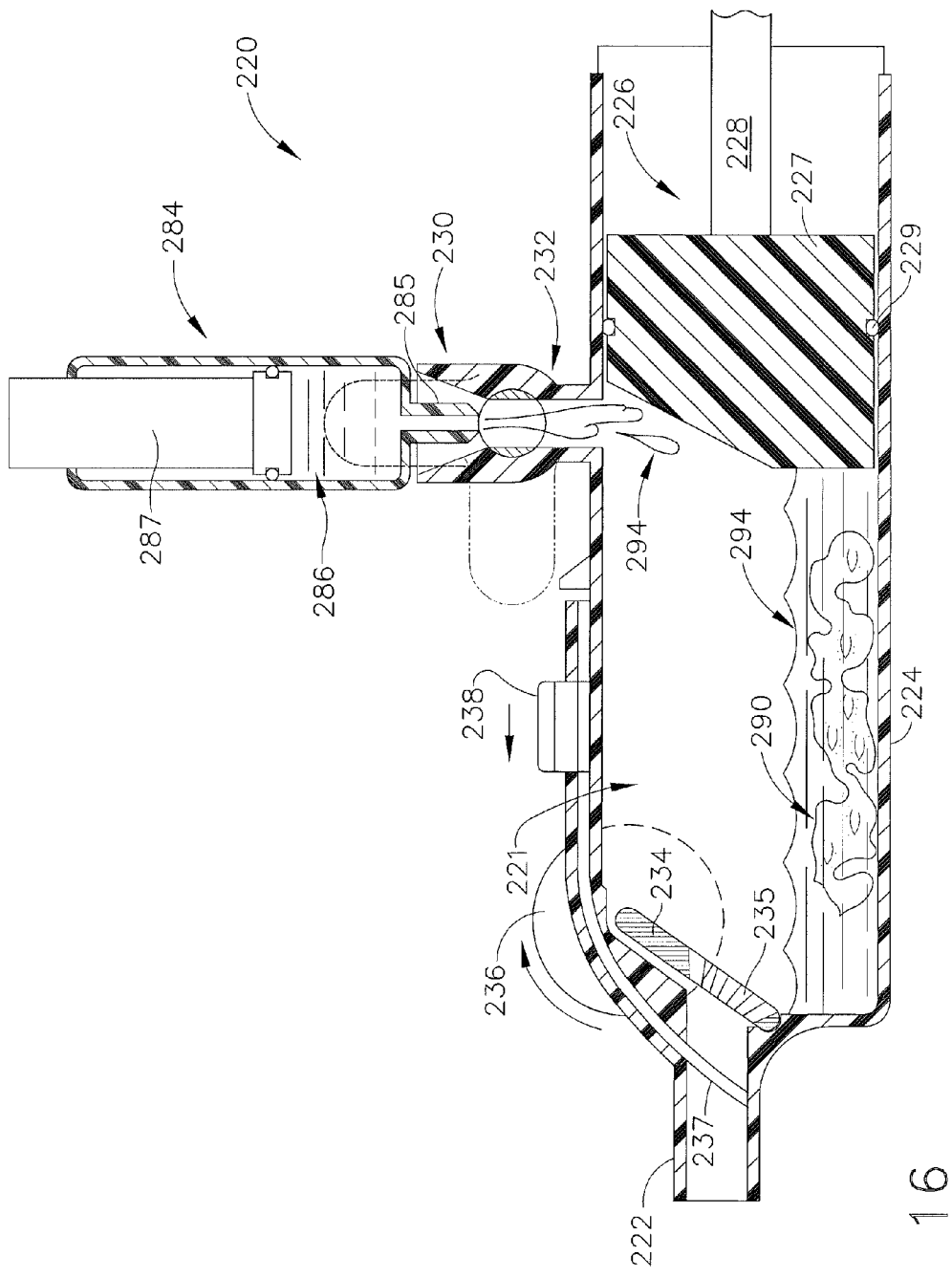
FIG. 16 depicts a side cross-sectional view of the tissue harvesting and mincing system of FIG. 15, with the mincing die in a mincing position and with fluid being introduced into the mixing chamber.

As shown in FIG. 16, an injector (284) may be coupled with port (232). In particular, injector (284) includes a port (285) that may be inserted into port (232). Port (285) is in fluid communication with a reservoir (286) defined by injector (284). A plunger (287) is longitudinally movable in injector (284) to inject a medical fluid component (294) from reservoir (286) of injector (284) into reservoir (221) of body portion (220) via ports (285, 232). It should be understood that injector (284) is merely on example. For instance, a conventional syringe or various other types of fluid injection devices may be used in lieu of injector (284). It should also be understood that reservoir (221) may be already provided with sufficient medical fluid (294) therein, such that introduction of additional medical fluid (294) into reservoir (221) is not necessary.

In an exemplary use of tissue harvesting and mincing device (200), needle adapter (240) is initially coupled with body portion (220). A distal portion of needle adapter (240) is inserted into a patient's tissue (e.g., thigh muscle, etc.). Tissue is then prolapsed through transverse aperture (254). In some versions, the prolapse of tissue is facilitated through activation of a vacuum source that is coupled with proximal end (257) of conduit (256). In some other versions, the prolapse of tissue is facilitated through proximal movement of piston (226) in housing (224), with proximal end (257) of conduit (256) being substantially sealed. Next, relative translation is provided between needle (250) and cutter (244), such as by sliding or holding block (262), such that distal edge (246) of cutter (244) severs a tissue core (290) from the prolapsed tissue as shown in FIG. 15. At this stage, a pressurized medium is communicated through conduit (256) while valve (230) is open in order to vent port (232), providing a pressure differential that transports tissue core (290) proximally through lumen (248) of cutter (244) toward reservoir (221). Also at this stage, slider (238) is at a proximal position to open gate (237) in order to provide free passage of tissue core (290) through port (222) into reservoir (221). In addition, mincing die (234) is rotated away at this stage to provide free passage of tissue core (290) into reservoir (221). In some other versions, mincing die (234) is rotated to a position between port (222) and reservoir (221), such that tissue core (290) must pass through mincing die (234) and be cut by mincing blades (235) before reaching reservoir (221). It should also be understood that, instead of using a pressurized medium to transport tissue core (290) proximally, piston (226) may be used to transport tissue core (290) proximally. In particular, with port (232) closed by valve (230), and with proximal end (257) of conduit (256) being vented to atmosphere, piston (226) may be pulled proximally through housing (224) to induce a vacuum at the proximal face of tissue core (290). Various other suitable ways in which tissue core (290) may be harvested from a patient and communicated to reservoir (221) will be apparent to those of ordinary skill in the art in view of the teachings herein.

Figure 17:
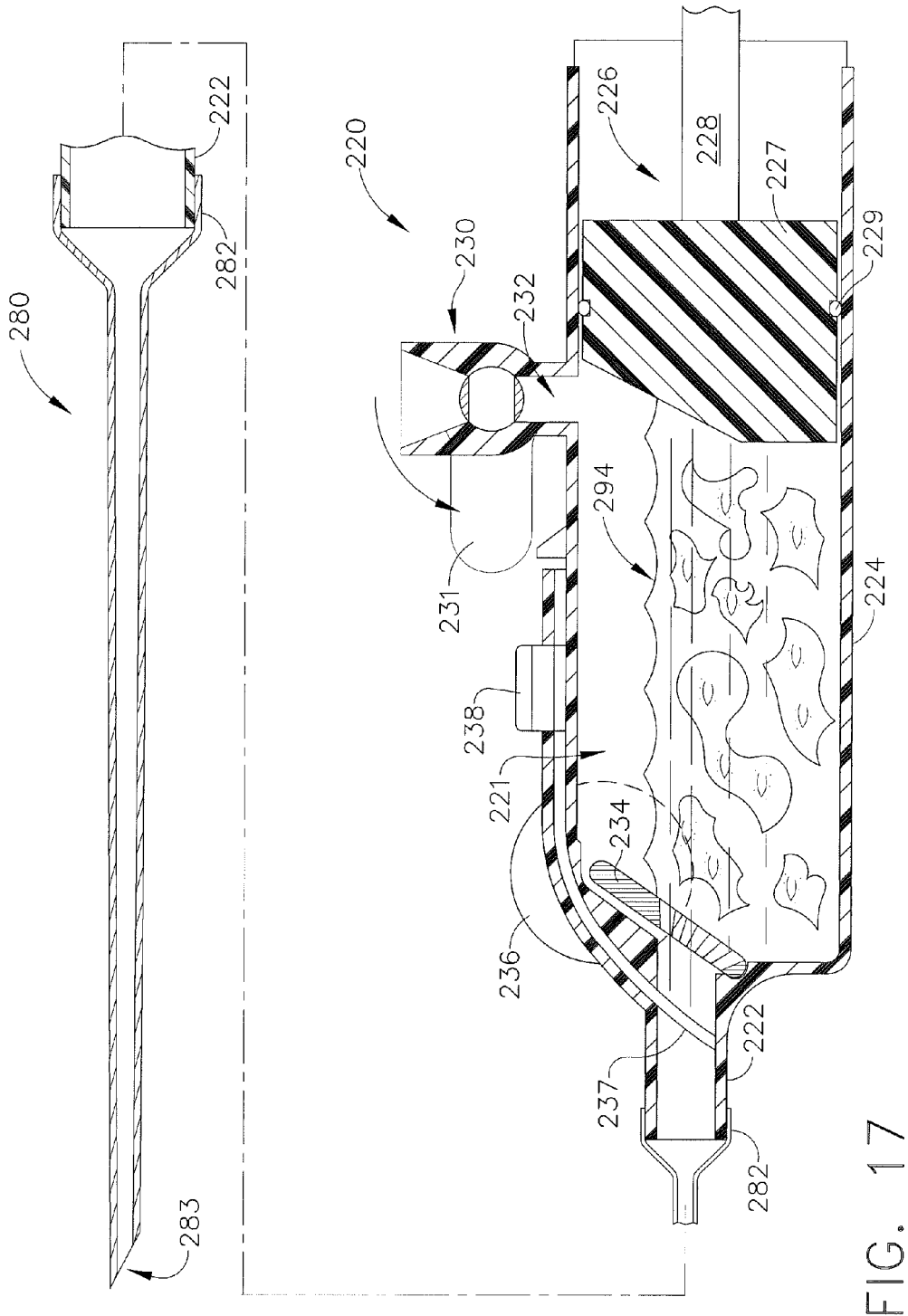
FIG. 17 depicts a side cross-sectional view of the tissue harvesting and mincing system of FIG. 15, with the mincing die in the mincing position, with the mixing chamber valve being closed, and with an exemplary medical fluid applier adapter tip.

In the present example, once tissue core (290) has reached reservoir (221), slider (238) is moved to a distal position to effectively close off port (222) with gate (237) as shown in FIG. 16. Needle adapter (240) is removed from body portion (220) at this stage. In addition, finger wheel (236) is rotated to position mincing die (234) between reservoir (221) and port (222). With valve (230) open, port (285) of injector (284) is inserted into port (232) of body portion (220). Plunger (287) is advanced to dispense a medical fluid component (294) into reservoir (221). Medical fluid component (294) may comprise any suitable medical fluid component described herein, among others. Once a suitable amount of medical fluid component (294) has been introduced into reservoir (221) with tissue, lever (231) is rotated to close valve (230), thereby substantially sealing off port (230) as shown in FIG. 17. Gate (237) remains closed at this stage. In addition, applier adapter (280) is coupled with body portion (220) at this stage, by inserting male port (222) in female port (282). As can be seen in FIGS. 16-17, tissue core (290) becomes irregular in shape, increases in volume, and breaks apart as it absorbs medical fluid component (294) in the present example. However, it should be understood that tissue core (290) may have any other suitable reaction(s) in the presence of a medical fluid component (294).

Figure 18:
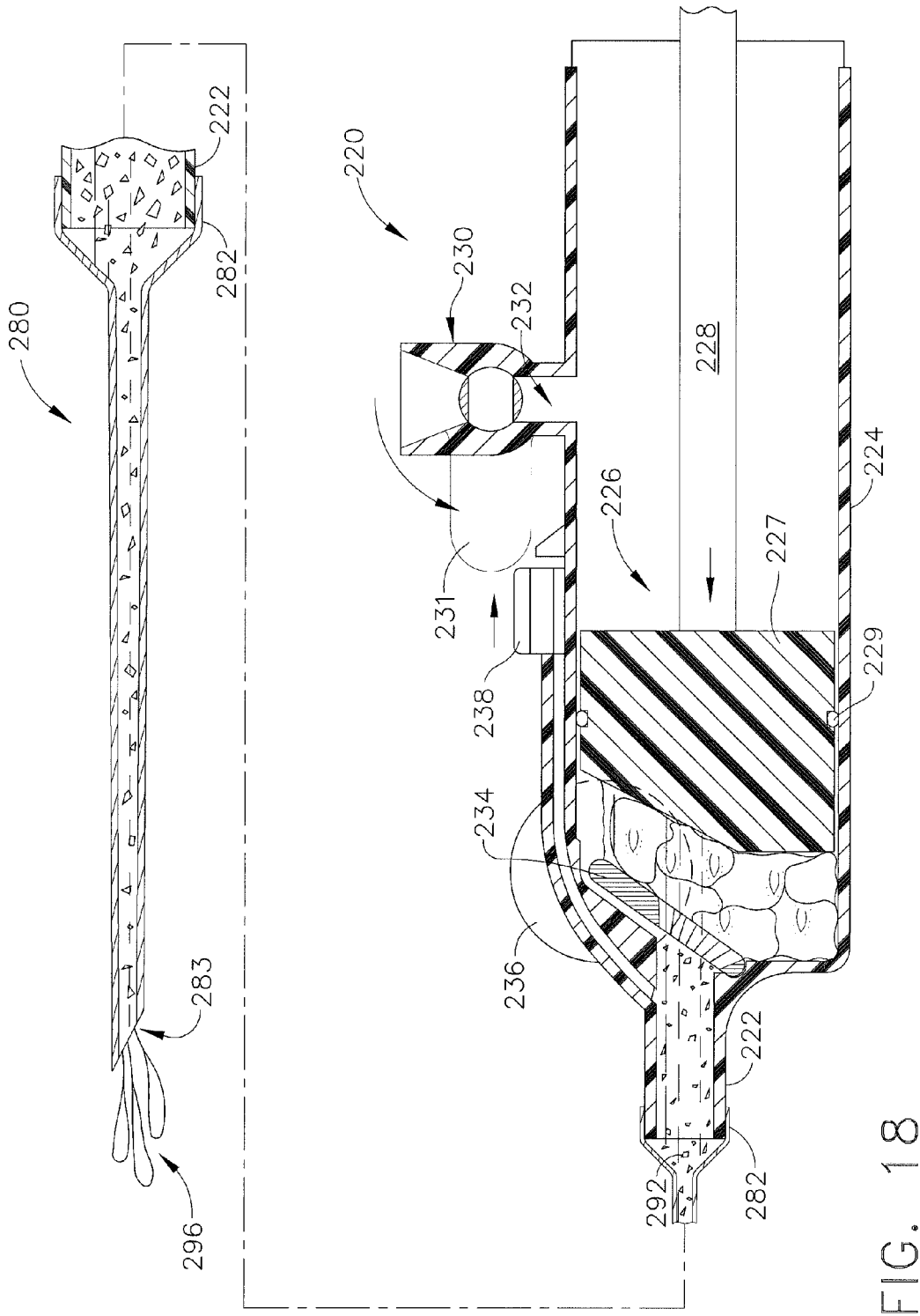
FIG. 18 depicts a side cross-sectional view of the tissue harvesting and mincing system of FIG. 15, with the mincing die in the mincing position and with a plunger being advanced distally to administer the mixed fluid.

Once applier adapter (280) is sufficiently coupled with body portion (220), gate (237) is raised by moving slider (238) proximally as shown in FIG. 18. Open distal end (283) of applier adapter (280) is positioned at the target site, such as a surgical site, an accidental trauma site, an anatomical defect (e.g., fistula, etc.), and/or any other suitable type of site. As is also shown in FIG. 18, piston (226) is advanced distally at this stage to reduce the effective volume defined by reservoir (221). As a result, tissue (290) and medical fluid component (294) are forced distally through mincing die (234). As tissue (290) is forced through mincing die (234), mincing blades (235) cut tissue (290) into minced tissue particles (292). Minced tissue particles (292) and medical fluid component (294) combine to form a medical fluid mixture (296), which is expelled through open distal end (283) of applier adapter (280) and in or onto the target site. In some other versions, needle adapter (240) remains coupled with body portion (220), and medical fluid mixture (296) is expelled directly through transverse aperture (254) at the target site, without adding applier adapter (280) to body portion (220). Various other suitable ways in which tissue harvesting and mincing device (200) may be made and used will be apparent to those of ordinary skill in the art in view of the teachings herein.

V. Exemplary Tissue Harvesting and Mincing Device Having a Mincing Blade

FIGS. 19-22 depict another exemplary tissue harvesting and mincing device (300). Tissue harvesting and mincing device (300) of this example includes a body portion (320) that may be selectively coupled with needle adapter (240) as described above. In particular, body portion (320) includes a male port (322) that is configured to be selectively coupled with female port (242) of needle adapter (240). Since needle adapter (240) has already been described above, the same details will not be repeated here. However, it should be understood that a variety of other components may be coupled with male port (322) as desired. In some versions, body portion (320) may also be selectively coupled with applier adapter (280) described above. For instance, needle adapter (240) may be removed from body portion (320) and applier adapter (280) may then be coupled with body portion (320) just like the switching of these components as described above with respect to body portion (220).

Body portion (320) of the present example further comprises a housing (324), a tissue press (330), a press actuator (340), a mincer (350), and a reservoir (360). Tissue press (330) is integrally mounted to a block (332) by a living hinge (334), and is resiliently biased to extend upwardly to receive tissue core (390) under its bottom surface (336). Bottom surface (336) is knurled in the present example to grip tissue core (390) during mincing of tissue core (390) as will be described in greater detail below. Block (332) is slidably disposed in housing (324), such that block (332) and tissue press (330) may be freely translated distally and proximally in housing (324).

Press actuator (340) is also integrally mounted to block (332) by a living hinge (342), and is resiliently biased to extend upwardly. Press actuator (340) includes a protrusion (344) on its underside and has a knurled upper surface (346) that may be engaged by a user's finger (e.g., thumb, etc.) during use to press downwardly on tissue press (330) and to slide tissue press (330) distally and proximally as will be described in greater detail below. In some other versions, tissue press (330) is configured such that a user may directly engage a top portion of the tissue press (330) with the user's finger, such that press actuator (340) may be omitted altogether.

Figure 19:
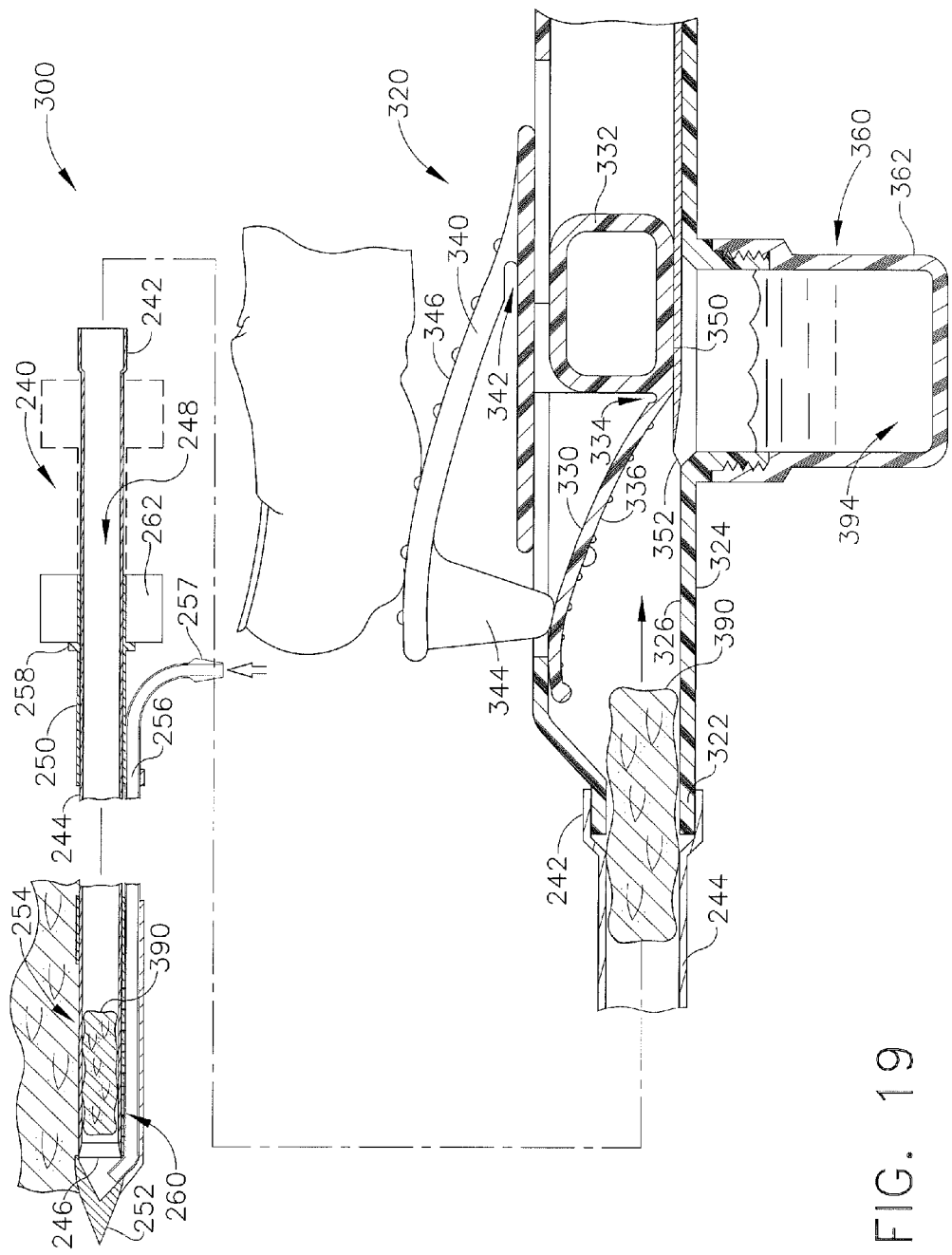
FIG. 19 depicts a side cross-sectional view of another exemplary tissue harvesting and mincing system, with a tissue specimen being communicated proximally toward a mincing blade.
Figure 20:
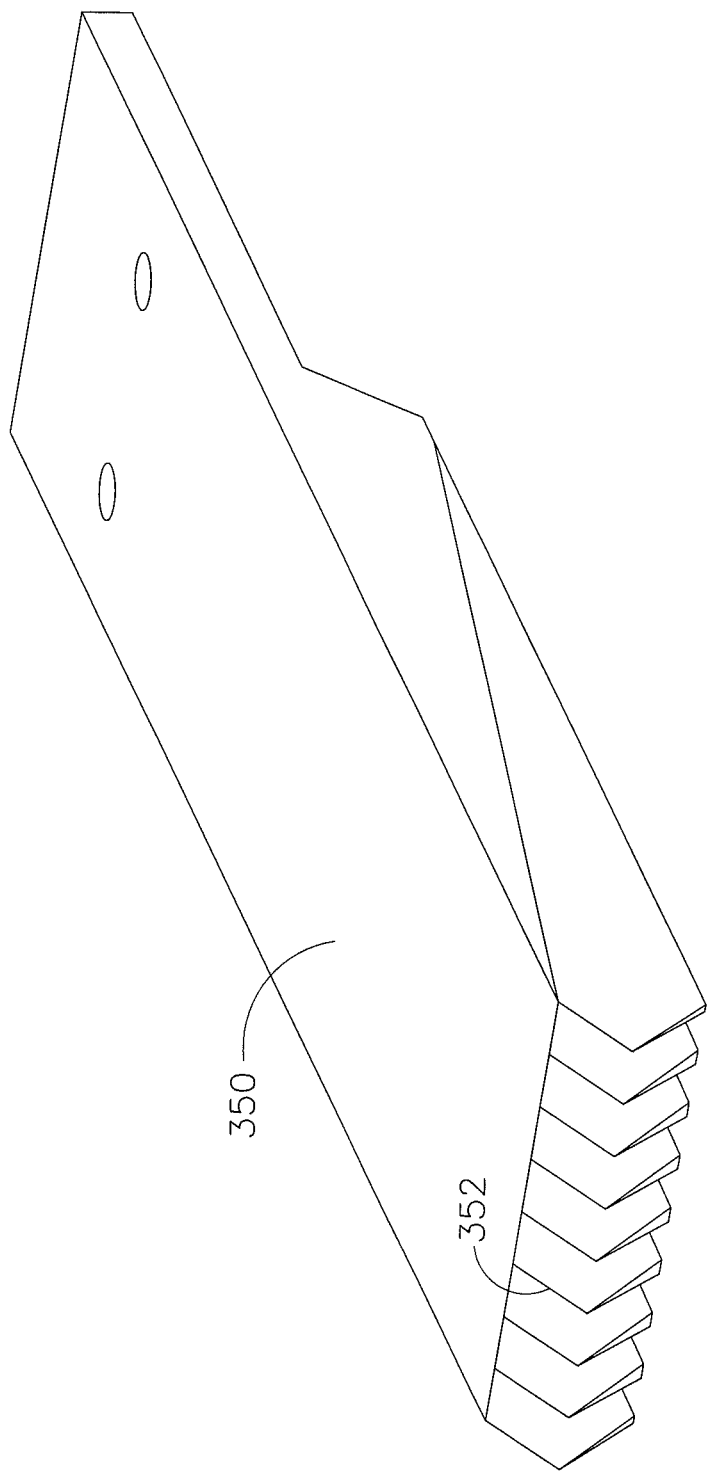
FIG. 20 depicts a perspective view of the mincing blade of the tissue harvesting and mincing system of FIG. 19.
Figure 21:
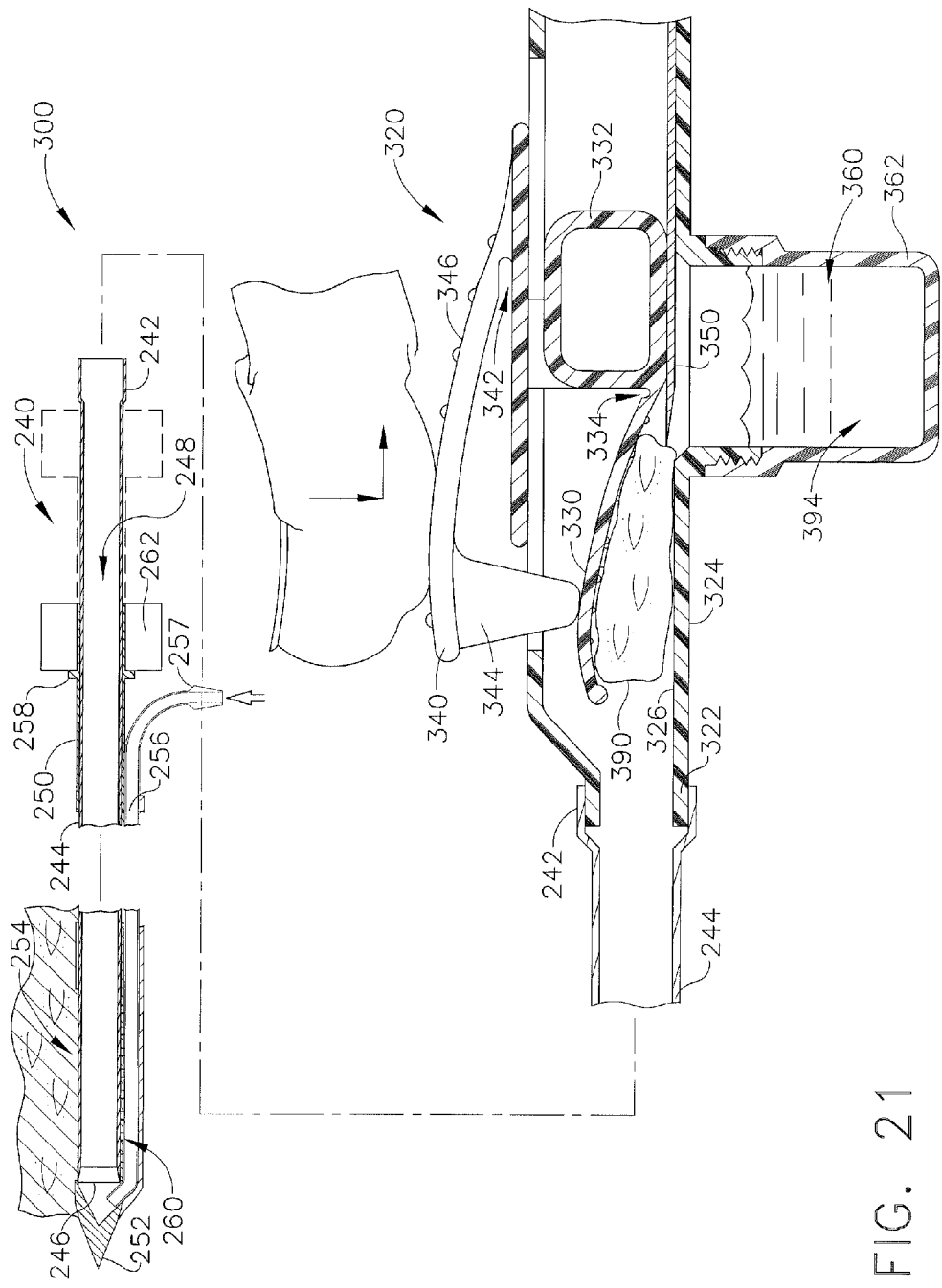
FIG. 21 depicts a side cross-sectional view of the tissue harvesting and mincing system of FIG. 19, with a tissue press being engaged to urge the tissue specimen into the mincing blade.
Figure 22:
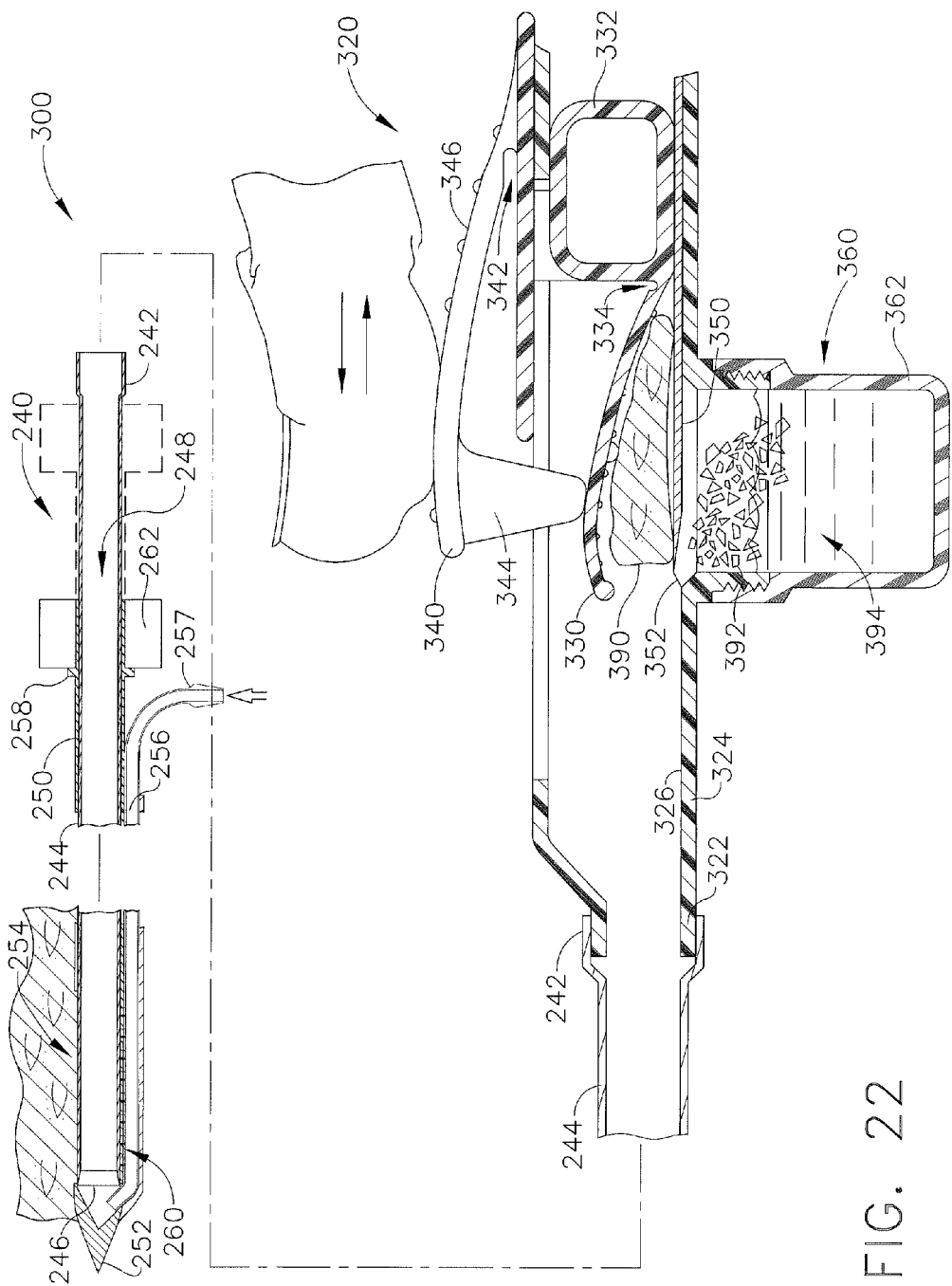
FIG. 22 depicts a side cross-sectional view of the tissue harvesting and mincing system of FIG. 19, with the tissue press being reciprocated to mince the tissue specimen with the mincing blade.

As best seen in FIG. 20, mincer (350) of the present example comprises a plurality of parallel vertical blades (352). Blades (352) are spaced and configured to mince tissue core (390) into minced tissue particles (392) as will be described in greater detail below. As can be seen in FIGS. 19 and 21-22, mincer (350) is sized and positioned in housing (324) such that portions of blades (352) extend above a lower interior surface (326) of housing (324). Mincer (350) is thus positioned relative to lower interior surface (326) in a manner similar to a blade of a mandoline type of food processing utensil. Of course, as with any other component described herein, mincer (350) may have any other suitable features, configuration, and/or positioning.

Reservoir (360) of the present example comprises a cup (362) containing a medical fluid component (394). Cup (362) is threadingly engaged with housing (324) in the present example, such that cup (362) may be selectively coupled with or removed from housing (324) as desired. A variety of other types of engagement may be used in lieu of threaded engagement, including but not limited to a bayonet mount, etc. As shown, reservoir (360) is positioned beneath mincer (350). Thus, as blades (352) of mincer (350) mince tissue core (390) into minced tissue particles (392), minced tissue particles (392) fall directly into medical fluid component (394) in reservoir (360).

In an exemplary use of tissue harvesting and mincing device (300), needle adapter (240) is coupled with body portion (320), and a distal portion of needle adapter (240) is inserted into a patient's tissue (e.g., thigh muscle, etc.). Tissue is then prolapsed through transverse aperture (254). In some versions, the prolapse of tissue is facilitated through activation of a vacuum source that is coupled with proximal end (257) of conduit (256). Next, relative translation is provided between needle (250) and cutter (244), such as by sliding or holding block (262), such that distal edge (246) of cutter (244) severs a tissue core (390) from the prolapsed tissue as shown in FIG. 19. At this stage, a pressurized medium is communicated through conduit (256) to transport tissue core (390) proximally through lumen (248) of cutter (244) toward tissue press (330). Various other suitable ways in which tissue core (390) may be harvested from a patient and communicated toward tissue press (330) will be apparent to those of ordinary skill in the art in view of the teachings herein.

Once tissue core (390) has reached tissue press (330) such that tissue core (390) is positioned underneath tissue press (330), a user engages upper surface (346) of press actuator (340) and presses downwardly as shown in FIG. 21. This downward force is communicated to tissue press (330) via protrusion (344), such that tissue core (390) is squeezed between bottom surface (336) of tissue press (330) and lower interior surface (326) of housing (324). While maintaining this downward force on tissue core (390), the user then repeatedly slides press actuator (340) distally and proximally as shown in FIG. 22. Due to the configuration and position of mincer (350) as well as the range of travel of tissue press (330), this repeated distal and proximal motion of tissue core (390) under a downward force causes tissue core (390) to be minced by blades (352). The resulting minced tissue particles (392) fall into medical fluid component (394) in reservoir (360) to produce a medical fluid mixture. The user may repeat the distal and proximal mincing motion until tissue core (390) becomes fully minced. Reservoir (360) may then be removed from housing (324), and the medical fluid mixture contained therein may be further processed or administered to a patient as described elsewhere herein. Various other suitable ways in which tissue harvesting and mincing device (300) may be made and used will be apparent to those of ordinary skill in the art in view of the teachings herein.

Figure 23:
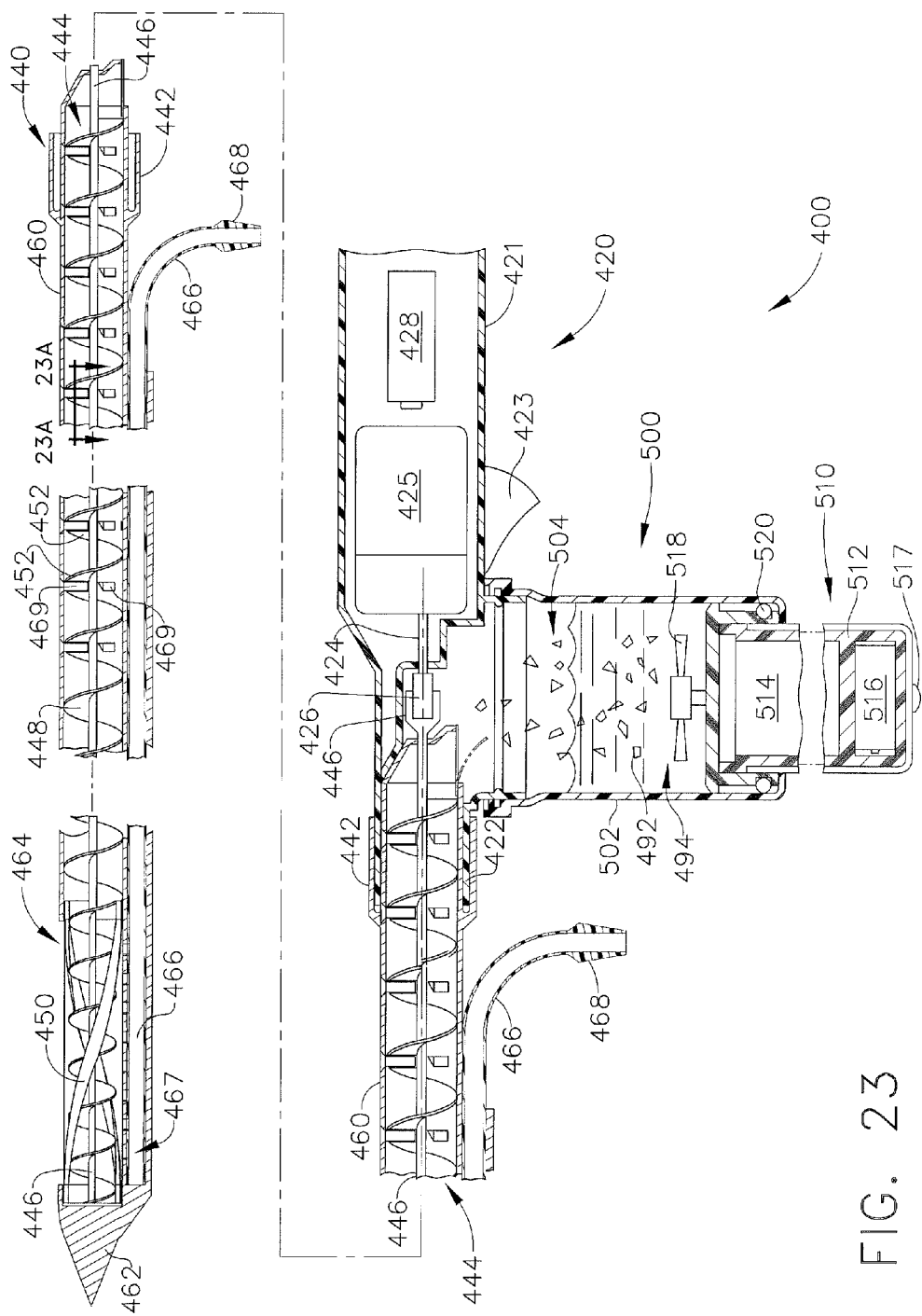
FIG. 23 depicts a side cross-sectional view of another exemplary tissue harvesting and mincing system, with a tissue harvesting tip secured to a body portion, and with a mixing piston in a lower position to provide a mixing volume in a mixing chamber.
Figure 24:
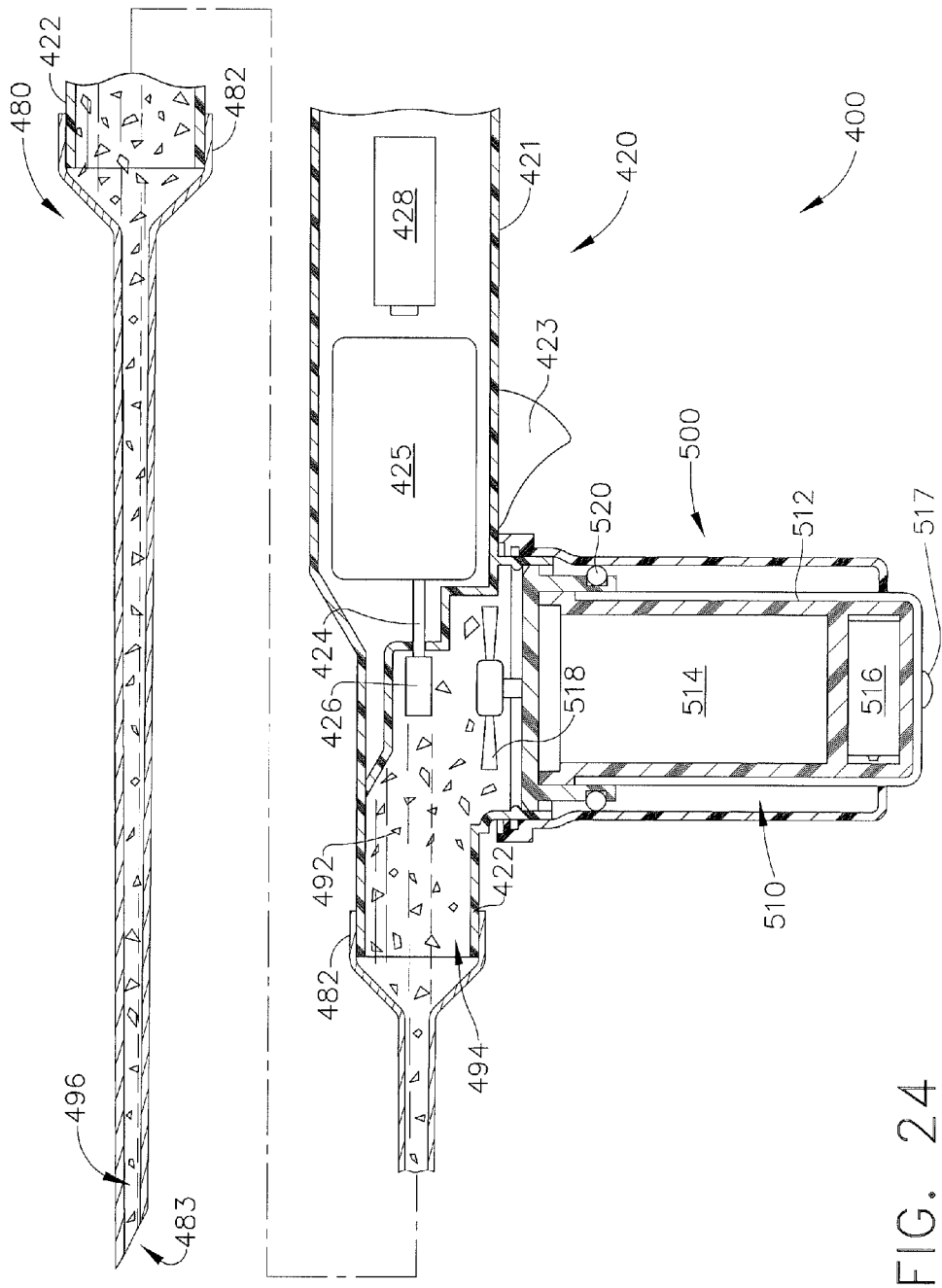
FIG. 24 depicts a side cross-sectional view of the tissue harvesting and mincing system of FIG. 23, with an applier tip secured to the body portion, and with the mixing piston in an upper position to urge a mixed medical fluid out through the applier tip.

VI. Exemplary Tissue Harvesting and Mincing Device Having Modular Tips and a Mixing Piston FIGS. 23-24 depict yet another exemplary tissue harvesting and mincing device (400). Tissue harvesting and mincing device (400) of this example includes a body portion (420), a needle adapter (440), and an applier adapter (480). Body portion (420) includes a male port (422) that is configured to be selectively coupled with a female port (442) of needle adapter (440) or a female port (482) of applier adapter (480). Other components of body portion (420) will be described in greater detail below. Needle adapter (440) of this example includes a cutting and mincing member (444) that is rotatably disposed within an outer needle (460). Outer needle (460) includes a closed distal tip (462), a transverse aperture (464), and a conduit (466). Distal tip (462) has a configuration similar to that of distal tip (44) described above. Conduit (466) is configured similar to conduit (142) described above, except that conduit (466) lacks distal opening (146). Instead, conduit (466) distally terminates in a proximal face of distal tip (462). A plurality of transverse openings (467) provide fluid communication between conduit (466) and the lumen in which cutting and mincing member (444) is disposed, similar to openings (148) described above. Of course, as with openings (148) described above, openings (467) may be omitted if desired.

Conduit (466) of the present example has a proximal end (468) that is suitable for coupling with a pressurized medium source (not shown). For instance, proximal end (468) of conduit (466) may be in communication with a pump, a charged air canister, a syringe, etc. The pressurized medium communicated through conduit (466) may comprise air, saline, a medical fluid component, and/or any other suitable type of medium. It should be understood that communication of a pressurized medium through conduit (466) may facilitate proximal communication of tissue through needle adapter (440) toward body portion (420) as will be described in greater detail below. It should also be understood that a vacuum may be communicated through conduit (466) to assist in prolapsing tissue through transverse aperture (464) before the tissue is severed from the patient and during the severing of tissue from the patient. Such a vacuum may be provided by a pump or syringe, etc., coupled with proximal end (468); and may be switched to a pressurized medium after the tissue has been severed. In some versions, conduit (466) simply provides a vent to atmosphere, and communicates neither a pressurized medium nor a vacuum. In still other versions, conduit (466) is simply omitted altogether.

Cutting and mincing member (444) of the present example comprises an elongate shaft (446) running along the length of cutting and mincing member (444). Cutting and mincing member (444) is rotatable within outer needle (460) via shaft (446) as will be described in greater detail below. A distal portion of cutting and mincing member (444) includes a conveying auger blade (448) that is wrapped about shaft (446). A pair of helical blades (450) are secured to a distal portion of conveying auger blade (448). Helical blades (450) have an effective longitudinal length and position corresponding with the length and position of transverse aperture (464). In addition, helical blades (450) are configured such that helical blades (450) will sever tissue that is prolapsed through transverse aperture (464) while shaft (446) is rotating. In particular, helical blades (450) cooperate with longitudinally extending lateral edges (not shown) of needle (460) that partially define transverse aperture (464), such as by shearing the tissue in a manner similar to a manual "reel mower" type of lawnmower blade shearing a blade of grass. Tissue pieces that are severed by helical blades (450) are conveyed proximally through needle (460) by conveying auger blade (488) while shaft (446) is rotating. Conveying auger blade (488) may also further cut these tissue pieces into smaller pieces. As noted above, proximal conveyance of tissue pieces through needle (460) may also be facilitated by communicating a pressurized medium through conduit (466), in addition to or in lieu of conveying auger blade (488) providing proximal conveyance of tissue pieces through needle (460).

Figure 23A:
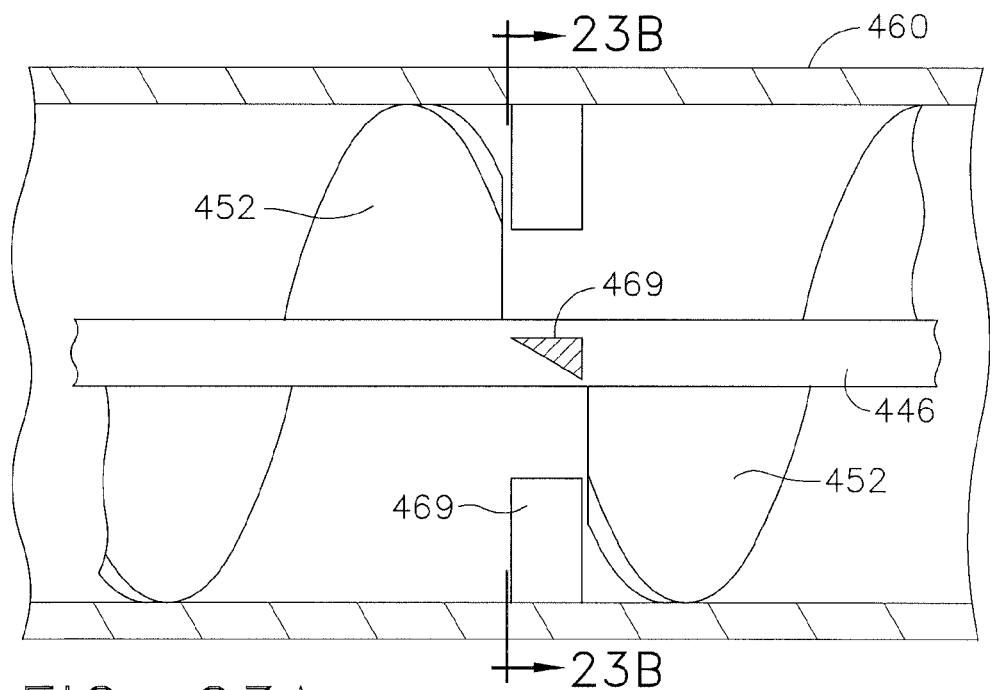
FIG. 23A depicts a cross-sectional view taken along line 23A-23A of FIG. 23
Figure 23B:
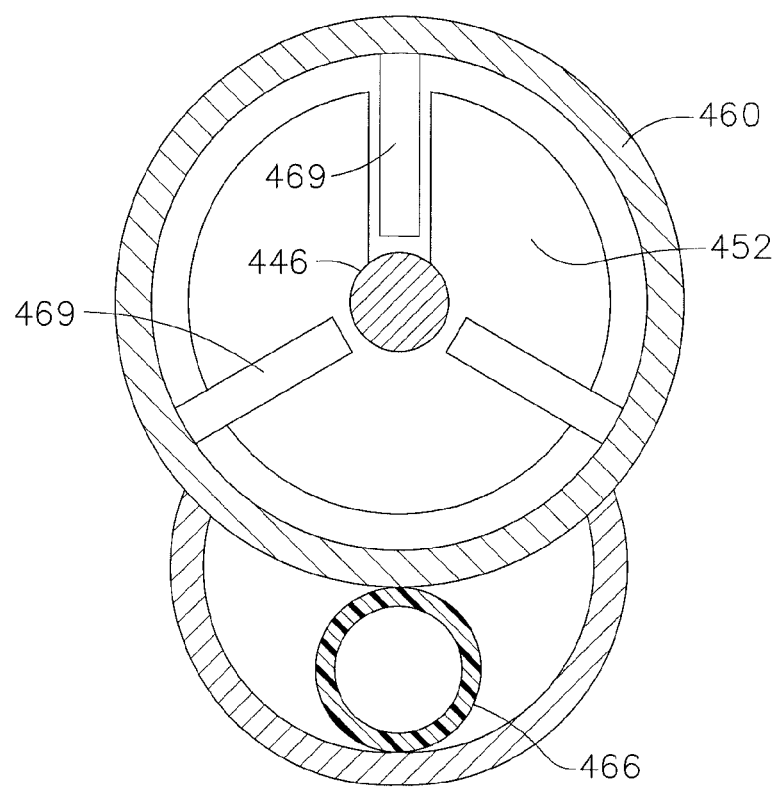
FIG. 23B depicts a cross-sectional view taken along line 23B-23B of FIG. 23A.

A proximal portion of cutting and mincing member (444) comprises a plurality of broken auger blade sections (452) that are disposed about shaft (446). Broken auger blade sections (452) are positioned along a length of cutting and mincing member (444) that corresponds with a length of outer needle (460) in which a plurality of projections (469) extend radially inwardly. In particular, and as best seen in FIGS. 23A-23B, projections (469) comprise inwardly projecting cutting pins that are fixed to outer needle (460), such that projections (469) remain stationary while cutting and mincing member (444) rotates within outer needle (460). As can be seen in FIG. 23A in particular, projections (469) are positioned at gaps between adjacent broken auger blade sections (452), such that projections (469) do not prevent cutting and mincing member (444) from rotating. In the present example, projections (469) are provided in sets of three at each gap between adjacent broken auger blade sections (452), with projections (469) in each set being equidistantly spaced from each other about the circumference of outer needle (460). Of course, any other suitable number of projections (469) may be provided at each gap between adjacent broken auger blade sections (452). As tissue is conveyed proximally through outer needle (460) while cutting and mincing member (444) rotates, projections (469) and broken auger blade sections (452) cooperate to mince the tissue, such that the tissue becomes further minced as it progresses proximally through the proximal portion of outer needle (460). In addition, broken auger blade sections (452) continue to convey the minced tissue proximally until the minced tissue ultimately reaches body portion (420). Of course, a variety of other components or features may be provided within the proximal portion of outer needle (460) to mince and/or convey tissue.

Body portion (420) of the present example comprises a housing (421), a motor (425), a battery (428), and a mixing chamber (500). Motor (425) includes a drive shaft (424) having a coupling (426) at its distal end. Coupling (426) is configured to releasably couple with a coupling (456) that is fixed to the proximal end of shaft (446). In particular, couplings (426, 446) are configured such that needle adapter (440) may be removably secured to body portion (420), with couplings (426, 446) being readily coupled upon coupling of needle adapter (440) with body portion (420), and with couplings (426, 446) being readily decoupled upon decoupling of needle adapter (440) from body portion (420). Various suitable configurations for couplings (426, 446) will be apparent to those of ordinary skill in the art in view of the teachings herein. When couplings (426, 446) are coupled, drive shaft (424) is operable to rotate shaft (446), thereby rotating cutting and mincing member (444). Battery (428) provides power to motor (425) to rotate drive shaft (424) in response to user actuation of trigger (423). While body portion (420) includes an integral power source in the form of battery (428), it should be understood that motor (425) may instead receive power from an external source. Similarly, it should be understood that shaft (446) may be rotationally driven in a variety of other ways, including but not limited to being driven manually (e.g., by a crank or dial, etc.). Various other suitable components and configurations that may be used to rotatingly drive shaft (446) will be apparent to those of ordinary skill in the art in view of the teachings herein.

Mixing chamber (500) of the present example comprises a reservoir housing (502) that is removably secured to housing (421) of body portion (420). Reservoir housing (502) defines a reservoir (504) containing a medical fluid component (494). Medical fluid component (494) may comprise any suitable medical fluid component described herein, among others. Reservoir (504) is positioned such that minced tissue particles (492) communicated proximally from needle adapter (440) will be deposited directly in reservoir (504). A piston mixer (510) is slidably disposed in reservoir housing (502). Piston mixer (510) comprises a body (512) containing a motor (514) and a battery (516). Motor (514) is operable to rotate a mixing blade (518), which is immersed in medical fluid component (494) in reservoir (504). Battery (516) provides power to motor (514). A switch (517) is operable to selectively couple battery (516) with motor (514). While body (512) includes an integral power source in the form of battery (516), it should be understood that motor (514) may instead receive power from an external source. Similarly, it should be understood that mixing blade (518) may be rotationally driven in a variety of other ways, including but not limited to being driven manually (e.g., by a crank or dial, etc.). Various other suitable components and configurations that may be used to rotatingly drive mixing blade (518) will be apparent to those of ordinary skill in the art in view of the teachings herein. Mixing blade (518) is configured to mix minced tissue particles (492) with medical fluid component (494) when mixing blade (518) is rotated.

An o-ring (520) is disposed about body (512) of piston mixer (510), and is configured to maintain a seal against the adjacent wall of reservoir housing (502). Body (512) of piston mixer (510) may be pushed upwardly to reduce the effective volume of reservoir (504), thereby expelling a medical fluid (496) comprising a mixture of minced tissue particles (492) and medical fluid component (494) from reservoir (504) as will be described in greater detail below. O-ring (520) is configured to maintain the seal against the adjacent wall of reservoir housing (502) as body (512) translates within reservoir housing (502).

Applier adapter (480) of the present example comprises a female port (482) at its proximal end and an open distal end (483). Female port (482) may provide a substantially snug fit against port (422) of body portion (420). Applier adapter (480) may be flexible, semi-flexible, rigid, or have any other suitable properties. As will be described in greater detail below, applier adapter (480) may be used to administer a medical fluid (496) to a target site in a patient.

In an exemplary use of tissue harvesting and mincing device (400), needle adapter (440) is initially coupled with body portion (420). A distal portion of needle adapter (440) is inserted into a patient's tissue (e.g., thigh muscle, etc.). Tissue is then prolapsed through transverse aperture (464). In some versions, the prolapse of tissue is facilitated through activation of a vacuum source that is coupled with proximal end (468) of conduit (466). In some other versions, the prolapse of tissue is facilitated through manual palpation of the patient's tissue into transverse aperture (464). Next, the user actuates trigger (423) to activate motor (425), which in turn rotates cutting and mincing member (444). Helical blades (450) then shear the prolapsed tissue, which is then communicated proximally through needle (460) by rotation of conveying auger blade (448). In some versions, proximal communication of sheared tissue through needle (460) is further provided at this stage by a pressurized medium communicated through conduit (466). The sheared tissue eventually reaches the length of needle (460) in which broken auger blade sections (452) and projections (469) are positioned. As cutting and mincing member (444) continues to rotate, the sheared tissue is minced by broken auger blade sections (452) and projections (469) into minced tissue particles (492). Minced tissue particles (492) are eventually communicated to reservoir (504) of mixing chamber (500). Various other suitable ways in which tissue may be harvested from a patient, minced, and communicated to reservoir (504) will be apparent to those of ordinary skill in the art in view of the teachings herein.

With minced tissue particles (492) in reservoir (504) of mixing chamber (500), the user releases trigger (423) and removes needle adapter (440) from body portion (420). The user then couples applier adapter (480) with body portion (420). Next, the user activates switch (517), which causes motor (514) to rotate mixing blade (518). Rotating mixing blade (518) mixes minced tissue particles (492) with medical fluid component (494) to form medical fluid mixture (496). Open distal end (483) of applier adapter (480) is then positioned at the target site, such as a surgical site, an accidental trauma site, an anatomical defect (e.g., fistula, etc.), and/or any other suitable type of site. With open distal end (483) of applier adapter (480) suitably positioned, the user pushes body (512) of piston mixer (510) upwardly in housing (502) of mixing chamber (500), thereby urging medical fluid mixture (496) distally through open distal end (483) of applier adapter (480) and in or onto the target site. In some other versions, needle adapter (440) remains coupled with body portion (420), and medical fluid mixture (496) is expelled directly through transverse aperture (464) at the target site, without adding applier adapter (480) to body portion (420). Various other suitable ways in which tissue harvesting and mincing device (400) may be made and used will be apparent to those of ordinary skill in the art in view of the teachings herein.

VII. Miscellaneous

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from suitable metals, ceramics, plastics, or combinations thereof. Furthermore, although not required, the construction of devices described herein may be configured to be compatible with or optimize their use with various imaging technologies. For instance, a device configured for use with MRI may be constructed from all non-ferromagnetic materials. Also for instance, when using optional imaging technologies with devices described herein, certain configurations may include modifications to materials of construction such that portions or the device may readily appear in a resultant image. Various suitable ways in which these and other modifications to the construction of devices described herein may be carried out will be apparent to those of ordinary skill in the art in view of the teachings herein.

Versions of the devices described above may have application in conventional medical treatments and procedures conducted by a medical professional, as well as application in robotic-assisted medical treatments and procedures.

Versions of described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A tissue harvesting and processing apparatus, the apparatus comprising:
   (a) a body;
   (b) a needle extending distally from the body, wherein the needle comprises a first lumen, wherein the needle defines a longitudinal axis, wherein the needle further defines an opening configured to receive prolapsed tissue, and wherein the first lumen is in communication with the opening;
   (c) a tissue cutting member disposed within the first lumen, wherein the tissue cutting member includes a mincing feature configured to simultaneously sever and mince tissue within the first lumen; and
   (d) a plunger member disposed within the first lumen proximally of the tissue cutting member, wherein the tissue cutting member is movable independently of the plunger member to mince a tissue specimen, and wherein the plunger member and the tissue cutting member are together movable to expel a mixture of tissue minced by the tissue cutting member with a medical fluid component through the opening.

2. The apparatus of claim 1, wherein the tissue cutting member comprises a disc having a plurality of openings.

3. The apparatus of claim 2, wherein the tissue cutting member further comprises a shaft, wherein the shaft extends along an axis that is parallel to the longitudinal axis defined by the needle, wherein the disc is mounted transversely to the shaft.

4. The apparatus of claim 3, wherein the plunger member defines a longitudinal bore, wherein the shaft extends through the longitudinal bore.

5. The apparatus of claim 2, further comprising an actuating member operable to reciprocate the disc within the needle to mince severed tissue.

6. The apparatus of claim 1, further comprising an applier adapter tip configured to removably couple with the needle, wherein the applier adapter tip comprises a distal opening configured to communicate minced tissue with a medical fluid component expelled by the plunger member into a site within a patient.

7. The apparatus of claim 1, wherein the tissue cutting member comprises a tube having a sharp distal edge.

8. The apparatus of claim 7, wherein the tissue cutting member further comprises at least one blade extending inwardly from the tube.

9. The apparatus of claim 1, wherein the needle comprises a needle adapter removably secured to a cannula, wherein the needle adapter has a closed distal end, wherein the closed distal end presents a sharp tip, wherein the cannula has a transverse aperture and an open distal end, wherein the closed distal end of the needle adapter is configured to block the open distal end of the cannula.

10. The apparatus of claim 9, further comprising an applier adapter tip configured to removably couple with the cannula in the absence of the needle adapter, wherein the applier adapter tip is configured to block the transverse aperture of the cannula, wherein the applier adapter tip comprises a distal opening configured to communicate a mixture of tissue minced by the tissue cutting member with a medical fluid component expelled by the plunger member through the open distal end of the cannula.

11. The apparatus of claim 1, wherein the plunger member is disposed within the tissue cutting member.

12. The apparatus of claim 1, wherein the needle has a closed distal end, wherein the opening configured to receive prolapsed tissue is transverse to the longitudinal axis defined by the needle, such that the longitudinal axis defined by the needle does not pass through the opening configured to receive prolapsed tissue.

13. The apparatus of claim 1, wherein the needle further comprises a second lumen, wherein the second lumen is parallel to the first lumen, wherein the first and second lumens are separated by a wall.

14. The apparatus of claim 13, wherein the wall includes a plurality of openings configured to provide fluid communication between the first and second lumens.

15. The apparatus of claim 1, wherein the body comprises a fluid reservoir containing a medical fluid component.

16. The apparatus of claim 15, further comprising a pressure pump operable to communicate the medical fluid component from the fluid reservoir to the needle.

17. A tissue harvesting and processing apparatus, the apparatus comprising:
  (a) a body;
  (b) a needle extending distally from the body, wherein the needle defines a longitudinal axis, wherein the needle further defines an opening configured to receive prolapsed tissue;
  (c) a tissue cutting member, wherein the cutting member comprises a tubular body and a first blade member and a second blade member secured to the tubular body, wherein the first blade member and the second blade member are secured to a distal end of the tissue cutting member, wherein the first blade member and the second blade member extend inwardly from an outer perimeter of the tubular body, wherein the first blade member and the second blade member are oriented transversely relative to a longitudinal axis defined by the tubular body, and wherein the tissue cutting member is configured to sever and mince tissue protruding through the opening of the needle;
  (d) a reservoir in fluid communication with the needle, wherein the reservoir is configured to hold a medical fluid component; and
  (e) a fluid expulsion component, wherein the fluid expulsion component is operable to expel a mixture of tissue minced by the tissue cutting member with a medical fluid component from the reservoir through the needle at a target site in a patient.

18. The apparatus of claim 17, wherein the fluid expulsion component comprises a plunger.

19. A method of harvesting and processing tissue using a tissue harvesting and processing instrument, wherein the tissue harvesting and processing instrument comprises a body, a needle having a distal end and an opening proximal to the distal end, a mincer operable to sever tissue protruding through the opening and mince severed tissue, a reservoir containing a medical fluid component, and an applier tip having a distal opening, the method comprising:
  (a) inserting the needle in a patient's tissue to protrudingly receive tissue through the opening of the needle;
  (b) severing a tissue specimen from tissue protruding through the opening of the needle, wherein the act of severing comprises actuating the mincer;
  (c) mincing the severed tissue specimen into minced tissue particles, wherein the act of mincing comprises actuating the mincer;
  (d) mixing the minced tissue particles with the medical fluid component from the reservoir to form a medical fluid mixture;
  (e) attaching the applier tip to the needle such that the distal opening of the applier tip is positioned distal to the distal end of the needle; and
  (f) expelling the medical fluid mixture through the distal opening of the applier tip at a target site in the patient.

* * * * *